(12) United States Patent
Leslie et al.

(10) Patent No.: US 8,323,893 B2
(45) Date of Patent: Dec. 4, 2012

(54) ADMINISTRATION OF EXOGENOUS MIRNA OR SIRNA

(75) Inventors: Christina S. Leslie, New York, NY (US); Debora S. Marks, Brookline, MA (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 12/907,966

(22) Filed: Oct. 19, 2010

(65) Prior Publication Data

US 2011/0092569 A1 Apr. 21, 2011

Related U.S. Application Data

(60) Provisional application No. 61/252,947, filed on Oct. 19, 2009.

(51) Int. Cl.
*C12Q 1/68* (2006.01)
*C12N 5/00* (2006.01)
*C12N 5/02* (2006.01)
*C12N 15/11* (2006.01)
*C07H 21/04* (2006.01)

(52) U.S. Cl. ........ 435/6.1; 435/325; 435/375; 536/24.5; 514/44 A

(58) Field of Classification Search ........................ None
See application file for complete search history.

(56) References Cited

U.S. PATENT DOCUMENTS

| 2009/0192111 A1* | 7/2009 | Bader et al. ...................... 514/44 |
| 2009/0192114 A1* | 7/2009 | Ovcharenko et al. ............ 514/44 |
| 2009/0232893 A1* | 9/2009 | Bader et al. .................... 424/489 |

OTHER PUBLICATIONS

Mertens-Talcott et al., 2007, Cancer Research, vol. 67, pp. 11001-11011.*
Krek et al., 2005, Nature Genetics, vol. 37, pp. 495-500.*
Huang et al., 2008, Nature Cell Biology, vol. 10, pp. 202-210. The reference also contains an attached supplementary table "Table S1a mcf7-373".*
Liu et al., 2007, Cellular & Molecular Immunology, vol. 4, pp. 59-63.*
Andrei L. Gartel, 2006, Molecular Cancer Therapy, vol. 5, pp. 1385-1386.*
Du et al., 2009, Molecular Cancer Research, vol. 7, pp. 1234-1243.*
Cao et al., 2008, Oncogene, vol. 27, pp. 7274-7284.*
Li et al., 2007, Biochemical and Biophysical Research Communications, vol. 363, pp. 165-170.*
Robbins, Marjorie et al. "Misinterpreting the Therapeutic Effects of Small Interfering RNA Caused by Immune Stimulation." Oct. 2008, pp. 991-999, vol. 19, Human Gene Therapy.
Rossi, John. "Wandering Eye for RNAi." Hune 2008, p. 611, vol. 14, No. 6, Nature Medicine.
Ruvkin, Gary. "The perfect storm of tiny RNAs." Oct. 2008, pp. xv-xix, vol. 14, No. 10, Nature Medicine.

Sandberg, Rickard et al. "Proliferating Cells Express mRNAs with Shortened 3' Untranslated Regions and Fewer MicroRNA Target Sites." 2008, pp. 1643-1647, vol. 320 Science.
Selbach, Matthias et al."Widespread changes in protein synthesis induced by microRNAs." Sep. 4, 2008, pp. 58-63, vol. 455, Macmillan Publishers Limited.
Shibata, M-A et al. "Combination therapy with Short interfering RNA vectors against VEGF-C and VEGF-A suppresses lymph node and lung metastasis in a mouse immunocompetent mammary cancer model." 2008, pp. 776-786, vol. 15, Cancer Gene Therapy.
Stenvang, Jan et al. "Targeting of microRNAs for therapeutics." 2008, pp. 1197-1200, vol. 36, Biochem. Soc. Trans.
Stewart, Candace et al. "Adverse effects induced by short hairpin RNA expression in porcine fetal fibroblasts." 2008, pp. 113-117, vol. 370, Biochemical and Biophysical Research Communications.
Tam, Wayne et al. "The emergent Role of MicroRNAs in Molecular Diagnostics of Cancer." Sep. 2008, pp. 411-414, vol. 10, No. 5, Journal of Molecular Diagnostics.
Vankoningsloo, Sebastien et al. "Gene expression silencing with 'specific' small interfering RNA goes beyond specificity—a study of key parameters to take into account in the onset of small interfering RNA off-target effects." 2008, pp. 2738-2753, vol. 275, The Authors Journal compilation.
Vella, Monica et al. "Architecture of a Calidated MicroRNA::Target Interaction." Dec. 2004, pp. 1619-1623, vol. 11, Chemistry and Biology.
Ventura, Andrea et al. "MicroRNAs and Cancer: Short RNAs go a Long Way." 2009, pp. 586-591, vol. 136, Cell.
Wargelius, Anna et al. "Double-Stranded RNA Induces Specific Developmental Defects in Zebrafish Embryos." 1999, pp. 156-161, vol. 263, Biochemical and Biophysical Research Communications.
Gruber, Jens et al. "RNAi of FACE1 protease results in growth inhibition of human cells expressing lamin A: implication for Hutchinson-Gilford progeria syndrome." 2005, pp. 689-696, vol. 118, Journal of Cell Science.
He, Lin et al. "MicroRNAs: Small RNAs with a Big Role in Gene Regulation." Jul. 2004, pp. 522-532, vol. 5, Cold Spring Harbor Laboratory.
He, Lin et al. "A microRNA component of the p53 tumour supressor network." Jun. 2007, pp. 1130-1135, vol. 447, Nature Publishing Group.
Jackson, Aimee et al. "Expression prolifing reveals off-target gene regulation by RNAi." Jun. 2003, pp. 635-637, vol. 21, No. 6, Nature Biotechnology. Jackson, Aimee et al. "Noise amidst the silence: off-targer effects of siRNAs?" Nov. 2004, pp. 521-524, vol. 20, No. 11, Trends in Genetics.
Jackson, Aimee et al. "Position-specific chemical modification of siRNAs reduces "off-target" transcript silencing." 2006, pp. 1197-1205, vol. 12, Cold Spring Harbor Laboratory Press.
Jackson, Aimee et al. "Widespread siRNA "off-target" transcript silencing mediated by seed region sequence complementarity." 2006, pp. 1179-1187, vol. 12, Cold Spring Harbor Laboratory Press.
John, Bino et al. "Human MicroRNA Targets." Nov. 2004, pp. 1862-1879, vol. 2, Issue 11, PLOS Biology.

(Continued)

*Primary Examiner* — Dana Shin
(74) *Attorney, Agent, or Firm* — Larson & Anderson, LLC

(57) ABSTRACT

Certain genes controlled by endogenous miRNA are actually upregulated upon the transfection of exogenous mi/siRNA. Based on this, methods of determining whether administration of mi/siRNA will have a deleterious effect by upregulating certain genes are provided. Comparison of sequences of exogenous mi/siRNA allows selection of exogenous miRNA to be administered to cell to enhance or limit this affect, and therefore to control unwanted disregulation, or to upregulate an endogenous miRNA-regulated gene of interest.

3 Claims, 8 Drawing Sheets

OTHER PUBLICATIONS

John, Matthias et al. "Effective RNAi-mediated gene silencing without interruption of the endogenous microRNA pathway." Oct. 11, 2007, pp. 745-748, vol. 449, Nature Publishing Group.

Krutzfeldt, Jan et al. "Silencing of microRNAs in vivo with antagomirs." Dec. 1, 2005, pp. 685-689, vol. 438, Nature Publishing Group.

Landgraf, Pablo et al. "A Mammalian microRNA Expression Atlas Based on Small RNA Library Sequencing." Jun. 29, 2007, pp. 1401-1414, vol. 129, Cell.

Leachman, Sancy et al. "Therapeutic siRNAs for dominant genetic skin diseases including pachyonychia congenita." Sep. 2008, pp. 151-157, vol. 51, No. 3, J Dermatol Sci.

Lim, Lee et al. "Microarray analysis shows that some microRNAs downregulate large numbers of target mRNAs." Feb. 17, 2005, pp. 769-773, vol. 433, Nature Publishing Group.

Linsley, Peter et al. "Transcripts Targeted by the MicroRNA-16 Family Cooperatively Regulate Cell Cycle Progression." Mar. 2007, pp. 2240-2252, vol. 27, No. 6, Molecular and Cellular Biology.

Lupberger, Joachim et al. "RNAi—A powerful tool to unravel hepatitis C virus-host interaction within the infectious life style." 2008, pp. 523-525, vol. 48, Journal of Hepatology.

Mayr, Christine et al. "Disrupting the Pairing Between let-7 and Hmga2 Enhances Oncogenic Transformation." Mar. 16, 2007, pp. 1576-1579, vol. 315, No. 5818, Science.

McBride, Jodi et al. "Artificial miRNAs mitigate shRNA-mediatred toxicity in the brain: Implications for the therapeutic development of RNAi." Apr. 15, 2008, pp. 5868-5873, vol. 105, No. 15, PNAS.

Oates, Andrew et al. "Too Much Interference: Injection of Double-Stranded RNA Has Nonspecific Effects in the Zebrafish Embryo." 2000, pp. 20-28, vol. 224, Developmental Biology.

Palliser, Deborah et al. "An siRNA-based microbicide protects mice from lethal herpes simplex virus 2 infection." Jan. 5, 2006, pp. 89-94, vol. 439, Nature Publishing Group.

Ambros, Victor. "The functions of animal microRNAs.", Sep. 16, 2004, pp. 350-355, vol. 431, Nature Publishing Group.

Baek et al. "The impact of microRNAs on protein output." Sep. 4, 2008, pp. 64-73, vol. 455, Macmillan Publishers Limited.

Bonci, Desiree et al. "The miR-15a-miR-16-1 cluster controls prostate cancer by targeting multiple oncogenic activities." Nov. 2008, pp. 1271-1277, vol. 14, No. 11, Nature Medicine.

Burchard, Julja et al. "MicroRNA-like off-target transcript regulation by siRNAs us species specific." 2009, pp. 308-315, vol. 15, Cold Spring Harbor Laboratory Press.

Castanotto, Daniela et al. "Combinatorial delivery of small interfering RNAs reduces RNAi efficacy by selective incorporation into RISC", 2007, pp. 5154-5164, vol. 35, No. 15, Nucleic Acids Research.

Chang, Tsung-Cheng et al. "Transactivation of miR-34a by p53 broadly influences gene expression and promotes apoptosis." Jun. 8, 2007, pp. 745-752, vol. 26, No. 5, Mol Cell.

Corsten, Maarten et al. "MicroRNA-21 Knockdown Disrupts Glioma Growth in vivo and Displays Synergistic Cytotoxicty with Neural Precursor Cell-Delivered S-TRAIL in Human Gliomas." Oct. 1, 2007, pp. 8994-9000, vol. 67, No. 19, Cancer Research.

Cummins, JM et al. "Implication of micro-RNA profiling for cancer diagnosis." 2006, pp. 6220-6227, vol. 25, Nature Publishing Group.

Cummins, Jordan et al. "The colorectal microRNAome." Mar. 7, 2006, pp. 3687-3692, vol. 103, No. 10 PNAS.

Didiano, Dominic et al. "Molecular architecture of a miRNA-regulated 3 UTR." 2008, pp. 1297-1317, vol. 14, Cold Spring Harbor Laboratory Press.

Elmen, Joacim et al. "Antagonism of microRNA-122 in mice by systemically administered LNA-antimiR leads to up-regulation of a large set of predicted target mRNAs in the liver." Dec. 23, 2007, pp. 1153-1162, vol. 36, No. 4, Nucleic Acids Research.

Elmen, Joacim et al. "LNA-mediated microRNA silencing in non-human primates." Apr. 17, 2008, pp. 896-900, vol. 452, Nature Publishing Group.

Fabani, Martin et al. "miR-122 targeting with LNA/29-O-methyl-oligonucleotide mixmers, peptide nucleic acids (PNA), and PNA-peptide conjugates." 2008, pp. 336-346, vol. 14, Cold Spring Harbor Laboratory Press.

Filipowicz, Witold et al. "Mechanisms of post-transcriptional regualtion by microRNAs: are the answers in sight." Feb. 2008, pp. 102-114, vol. 9, Nature Publishing Group.

Futreal, P. Andrew et al. "A Census of Human Cancer Genes." Mar. 2004, pp. 177-183, vol. 4, Nature Reviews.

Gauthier, Nicholas et al. "Cyckebase.org—a comprehensive multi-organism online database of cell-cycle experiments." 2008, pp. D854-D859, vol. 36, Nucleic Acids Research.

Grimm, Dirk et al. "Fatality in mice due to oversaturation of cellular microRNA/short hairpin RNA pathways." May 25, 2006, pp. 537-541, vol. 441, Nature Publishing Group.

Grimson, Andrew et al. "MicroRNA Targeting Specificity in Mammals: Determinants beyond Seed Pairing." Jul. 6, 2007, pp. 91-105, vol. 27, Molecular Cell.

* cited by examiner

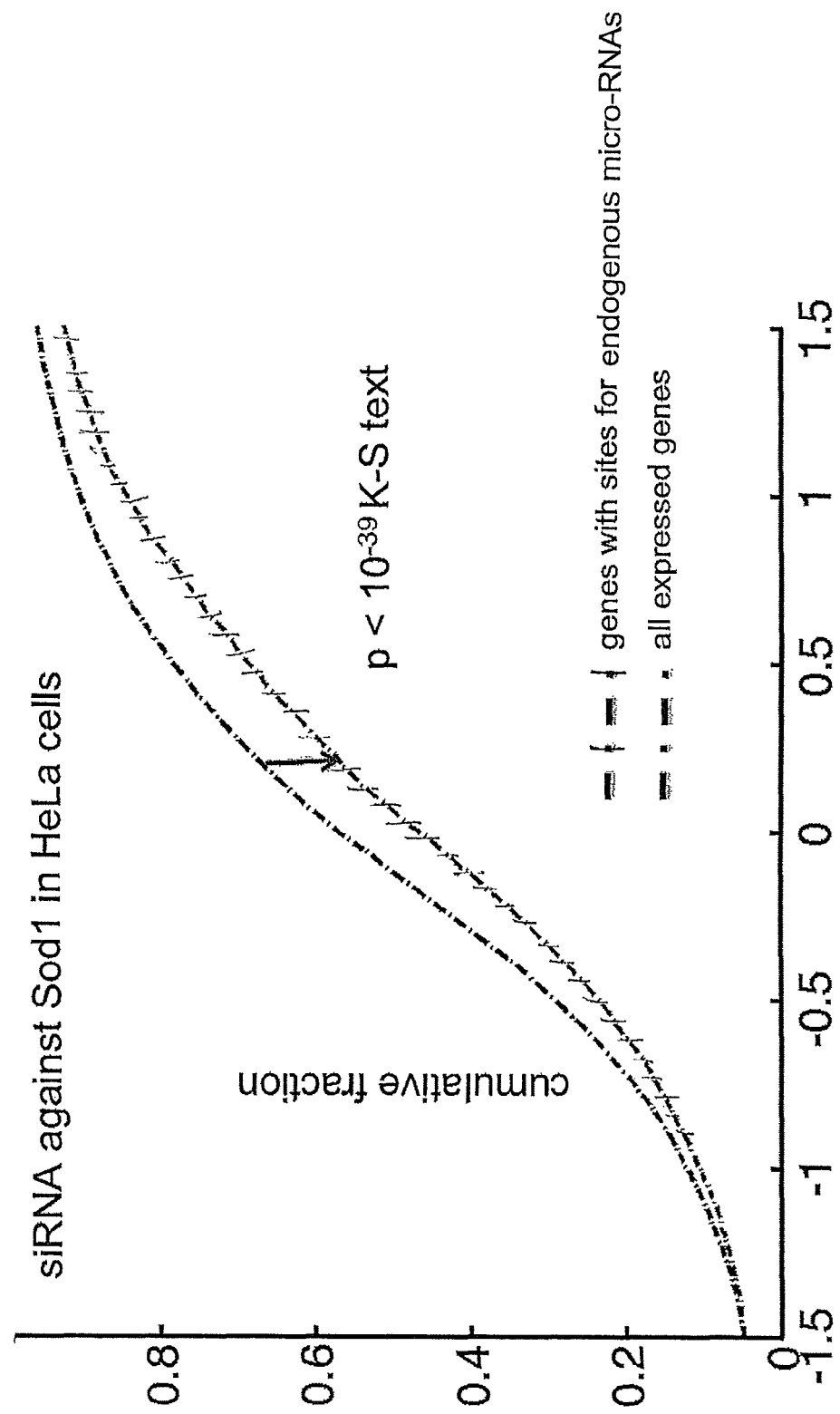

SEQUENCE LISTING

```
<160> NUMBER OF SEQ ID NOS: 10

<210> SEQ ID NO 1
<211> LENGTH: 22
<212> TYPE: DNA
<213> ORGANISM: Homo sapiens

<400> SEQUENCE: 1
tggagtgtga caatggtgtt tg                                                 22

<210> SEQ ID NO 2
<211> LENGTH: 22
<212> TYPE: DNA
<213> ORGANISM: Homo sapiens

<400> SEQUENCE: 2
tagcttatca gactgatgtt ga                                                 22

<210> SEQ ID NO 3
<211> LENGTH: 22
<212> TYPE: DNA
<213> ORGANISM: Homo sapiens

<400> SEQUENCE: 3
tagcagcacg taaatattgg cg                                                 22

<210> SEQ ID NO 4
<211> LENGTH: 22
<212> TYPE: DNA
<213> ORGANISM: Homo sapiens

<400> SEQUENCE: 4
cagtgcaatg ttaaaagggc at                                                 22
```

```
<210> SEQ ID NO 5
<211> LENGTH: 22
<212> TYPE: DNA
<213> ORGANISM: Homo sapiens

<400> SEQUENCE: 5
tggctcagtt cagcaggaac ag                                              22

<210> SEQ ID NO 6
<211> LENGTH: 22
<212> TYPE: DNA
<213> ORGANISM: Homo sapiens

<400> SEQUENCE: 6
aagctgccag ttgaagaact gt                                              22

<210> SEQ ID NO 7
<211> LENGTH: 21
<212> TYPE: DNA
<213> ORGANISM: Homo sapiens

<400> SEQUENCE: 7
ttcacagtgg ctaagttctg c                                               21

<210> SEQ ID NO 8
<211> LENGTH: 22
<212> TYPE: DNA
<213> ORGANISM: Homo sapiens

<400> SEQUENCE: 8
ttcaagtaat ccaggatagg ct                                              22

<210> SEQ ID NO 9
<211> LENGTH: 23
<212> TYPE: DNA
<213> ORGANISM: Homo sapiens

<400> SEQUENCE: 9
caacggaatc ccaaaagcag ctg                                             23

<210> SEQ ID NO 10
<211> LENGTH: 21
<212> TYPE: DNA
<213> ORGANISM: Homo sapiens

<400> SEQUENCE: 10
ctgacctatg aattgacagc c                                               21
```

ADMINISTRATION OF EXOGENOUS MIRNA OR SIRNA

STATEMENT OF RELATED CASES

This application claims the benefit under 35 USC §119 of U.S. Provisional Application No. 61/252,947 filed Oct. 19, 2009, which application is incorporated herein by reference in its entirety.

BACKGROUND OF THE INVENTION

Thousands of microRNAs (21-23 nt ssRNAs) have been identified in animals in the past years [1,2]. Subsequent research on miRNAs has focused on their biochemical processing and mechanism of action [3], the scope of their regulatory programs and their differential expression profiles in development and disease [4]. Furthermore, various si/miRNA constructs are widely used in functional genomics, miRNA cellular/tissue profiles are measured in medical diagnostics [5], and si/miRNAs (and their inhibitors) are in clinical trials for use as medical therapeutics [6, 7].

SUMMARY OF THE INVENTION

The present invention is based on the observation that transfection of small RNAs (si/miRNAs) into cells, which typically lowers expression of certain genes, unexpectedly increases expression of some genes controlled by endogenous miRNA. The specific genes enhanced by this mechanism are dependent on cell type, although some types of genes such as cell cycle genes may be common across multiple cell types. Enhanced genes for any given cell type can be routinely determined experimentally using the techniques in this application.

The genes controlled by endogenous miRNA can regulate oncogenes or cell cycle genes. In some cell types, notably the HeLa cells tested in the examples below, examples of regulated genes include: CCND1, SREBF1, DUSP4, DUSP5, ATF3, HMGA2, SCMLZ, TNRC6, YOD1, CX3CL1, AKAP12, SSR3, PLSCR4, and PTRF.

In one embodiment, the invention provides a method of choosing an exogenous mi/siRNA sequence to be applied to a cell for the purpose of downregulating a selected gene that takes into account endogenous miRNA target sequence(s). It is known in the art that number of endogenous miRNA sequences that are actually expressed in any given cell type is small compared to the total number of miRNA sequences that have been identified, and that in many cell types, a substantial majority of the miRNA in the cell is one of less than 10 types. In accordance with the method, an exogenous mi/siRNA sequence is chosen that will target genes that contain the endogenous miRNA target sequence of these more common miRNAs as well as the selected targets of the exogenous mi/siRNA sequence, for example as a consequence of sequence similarity with the seed region of the endogenous miRNA. This type of off-target silencing by siRNA has been discussed in the art, for example in "Widespread siRNA "off-target" transcript silencing mediated by seed region sequence complementarity", Jackson et al. (2006) RNA (7):1179-87.

In many cases, the sequences of genes and the endogenous miRNA that targets them are known, and the sequence of the selected gene is known in order to design the exogenous mi/siRNA, this may be a simple comparison of preexisting information. This method may be performed by determining the sequence of genes that are targeted by said endogenous miRNA sequence in a particular sample and choosing an mi/siRNA based on this determination.

In addition to guiding the selection of mi/siRNA for therapeutic purposes, knowledge of the disregulation that can follow from mi/siRNA therapies leads to therapeutic options. For example, an individual receiving mi/siRNA therapy could be tested for disregulation and then treated, for example using a secondary therapeutic such as an antisense or siRNA therapeutic targeted to the up-regulated gene. In the alternative, where it is established that up-regulation of a gene is a likely consequence, the treatment may be provided prophylactically without the initial testing.

In the case were testing is to be performed, the testing may be performed using a kit. In one embodiment, such a kit comprises a marker for endogenous miRNA regulated genes that facilitates the expression level of these genes in a tested sample. For specific cell types, the kit may include a plurality of markers for a plurality of genes overexpressed in that cell type. In specific embodiments, the kit also includes a sequence comparator to identify those endogenous miRNA regulated genes with and without a sequence match the exogenous mi/siRNA. In an embodiment, this kit includes reagents for delivering exogenous mi/siRNA sequences to a cell, for example exogenous sequences that the downregulate the overexpressed genes.

As administration of mi/siRNA may result in unwanted upregulation, the present invention teaches method for determining the potential for unwanted upregulation of genes as a result of mi/siRNA treatment on a cell comprising determining the number of endogenous miRNA target sites on genes expressed by the cell and correlating a relatively higher number of endogenous miRNA target sites with a higher likelihood of unwanted upregulation of genes containing endogenous miRNA target sites. This method also further involves determining endogenous miRNA expressed by the cell.

Also taught is a method for determining a dosage of exogenous mi/siRNA administered to a cell to reduce unwanted endogenous upregulation by determining the number of endogenous miRNA target sites on genes expressed by the cell and administering an amount of exogenous mi/siRNA consistent with the number of endogenous wherein less mi/siRNA is administered if more endogenous miRNA target sites are found.

As a skilled practitioner may desire upregulation of a gene controlled by endogenous miRNA, the invention also provide a method comprising the steps of determining which endogenous miRNA are expressed by the cell, determining whether a desirable gene has sites targeted by the endogenous miRNA, thereby determining that the gene is controlled by endogenous miRNA and administering an exogenous mi/siRNA that does not target the desirable gene, in a sufficient amount to upregulate the gene.

BRIEF DESCRIPTION OF THE DRAWINGS

FIG. 7 shows that siRNAs directed against Sod1 result in the significant upregulation of endogenously microRNA-controlled genes.

DETAILED DESCRIPTION OF THE INVENTION

The inventors have discovered that administration of mi/siRNA has the effect of upregulating genes controlled by endogenous miRNA regulation. This effect is observable both at the mRNA and protein levels; and it occurs following transfection of siRNAs designed to inhibit particular genes, as well as miRNA mimics and miRNA inhibitors introduced to test the biological effects of miRNAs.

Figure 1:
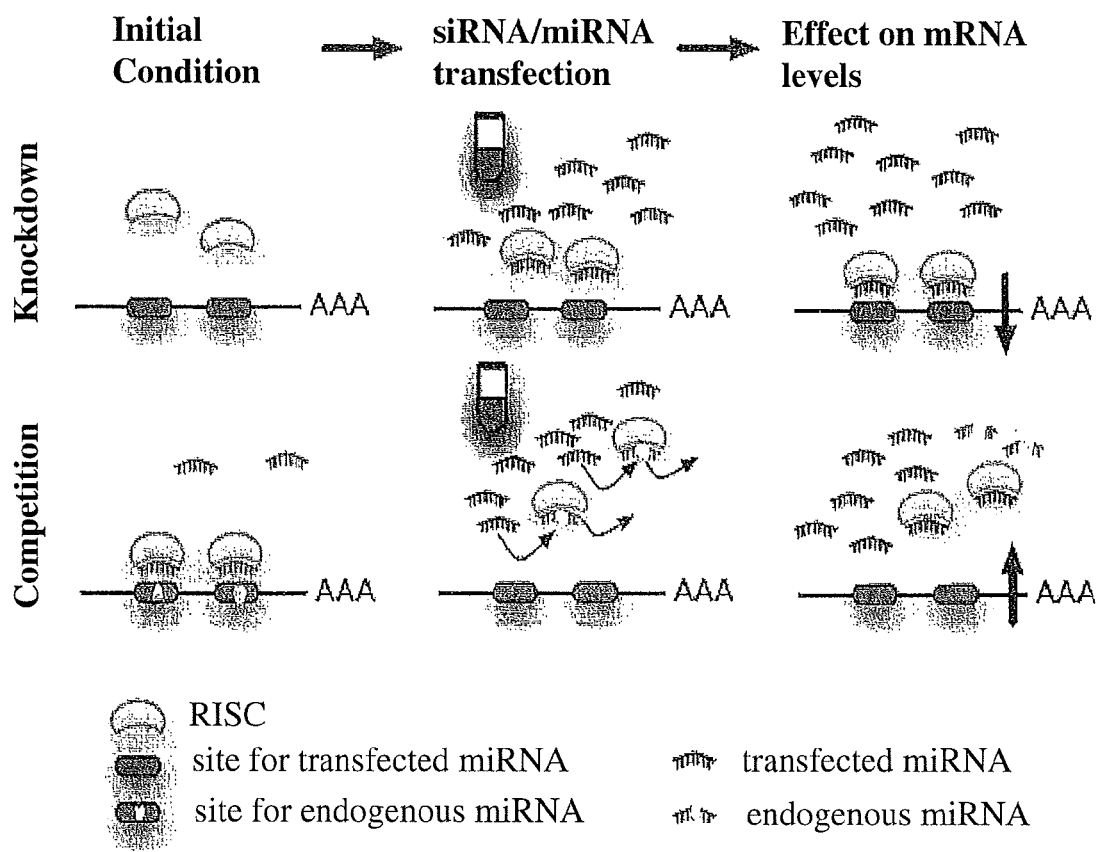
FIG. 1 shows model of competition for RISC machinery between transfected si/miRNA and the cell's endogenous miRNAs.
Figure 2:
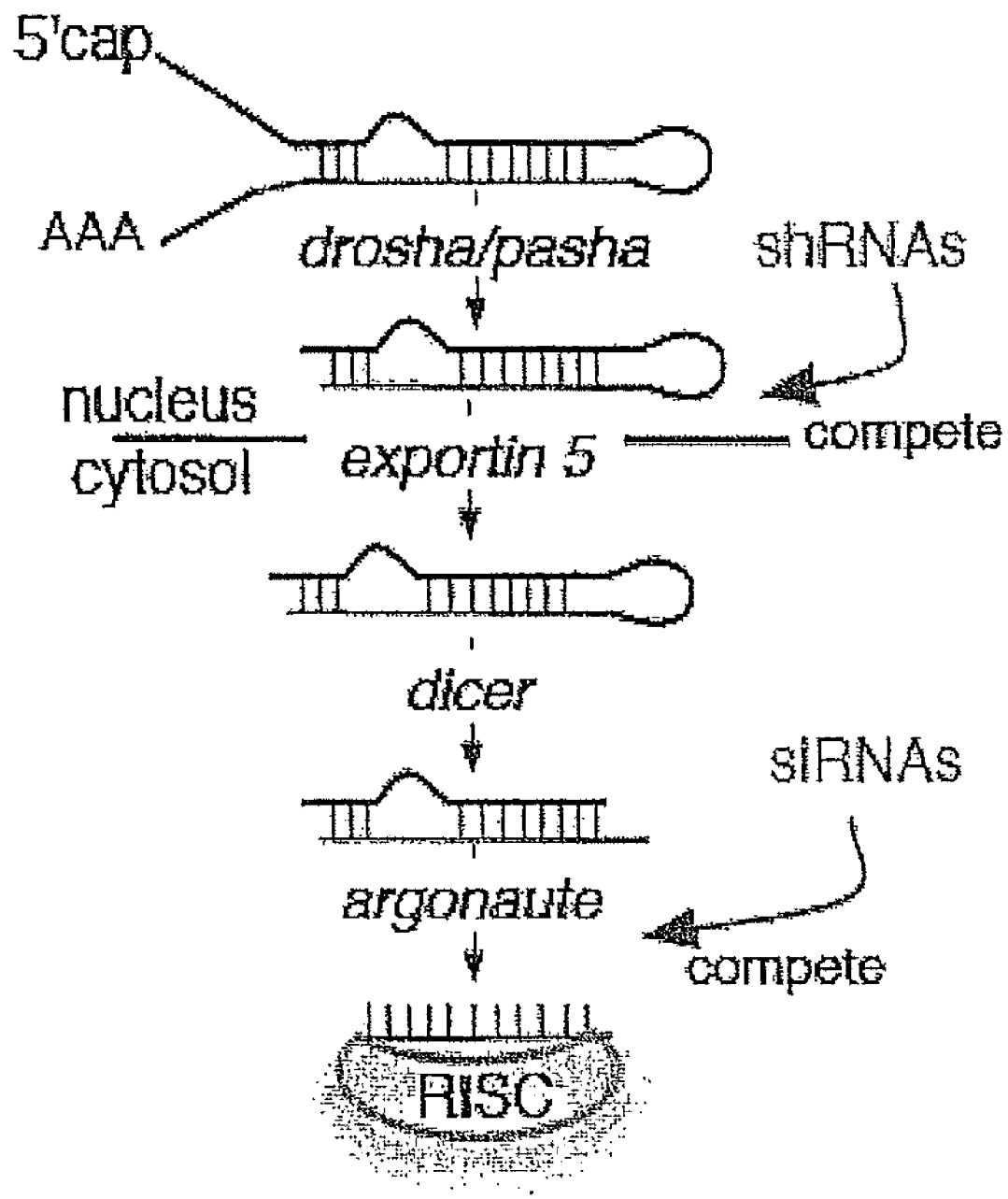
FIG. 2 shows the biogenesis of miRNAs to show where sh- and siRNAs enter the miRNA processing pathway.

Without intending to be bound by any particular mechanism, it appears that the unexplained upregulation of genes in si/miRNA transfections is due, at least partly, to a loss of function of the endogenous miRNAs, as modeled in FIG. 1 and consistent with reports suggesting machinery saturation [14]. In this model, the transfected small RNAs must compete with the endogenous miRNAs for the RISC complex (RNA-induced silencing complex) or other machinery further downstream than exportin 5 in the miRNA pathway, e.g. Argonaute proteins or TRBP [14-17]. Loss of available RISC through competition will relieve the repression of target genes of endogenous miRNAs and upregulate the corresponding mRNAs and proteins.

Knowledge of this phenomenon leads to various useful methods. This includes identification of endogenous sequences that control target genes within the cell, and the finding that administration of exogenous mi/siRNA may actually upregulate these controlled genes. With this knowledge, a skilled practitioner may actually upregulate a controlled gene, if so desired.

To test this hypothesis, we examined more than 150 miRNA and siRNA transfection experiments in 7 different cell lines. We reasoned that if endogenous miRNA activity is altered, we should be able to detect this effect in gene expression profiles taken after si/miRNA perturbations, even though no significance was afforded the effect in the original study. Finally, if our hypothesis is correct, we should see similar dose response and dynamics of these upregulated genes as for the downregulated target/off-target genes (but in the opposite direction) [18, 19].

Our results show that (i) genes with sites for endogenous miRNAs are significantly upregulated after the transfections, at both the mRNA and protein level, when compared to genes with neither endogenous nor transfected miRNA sites; (ii) genes with sites for the transfected si/miRNAs are more likely to be downregulated if they do not contain sites for endogenous miRNAs; (iii) a regression model can be used to predict these shifts in gene expression from the number and type of miRNA sites in the affected genes; (iv) the transfection dose response of genes with sites for endogenous miRNAs is similar to that of the downregulated genes; and (v) the temporal response of genes with sites for endogenous miRNAs is similar to that of the genes with sites for the transfected si/miRNAs. Our results also highlight specific examples of genes that are consistently upregulated in certain cell types after transfections, including the oncogene HMGA2 and genes involved in cell cycle regulation.

DEFINITIONS

As used in the specification and paragraphs of this application, the following terms are used and should be understood as follows:

"Endogenous miRNA" is miRNA produced by the cell. Different cell types may express different types and amounts of each miRNA.

"Sequence match", when comparing miRNA sequences to mi/siRNA sequences means that a person skilled in the art would reasonably understand that two sequences are similar enough to be likely to have the same inhibitory effect through RNAi. As is known in the art, the critical region of match is in the "seed region" found at bases 2-8 of the sequence. An exact complementary match is the most reliable indicator, because a higher degree of similarity leads to a higher confidence of similar activity. However, an exact match is not necessary. In preferred embodiments, a sequence match of at least six perfectly complementary bases within the seed region, more preferably at least 7 perfectly complementary bases is used as an indicator of a sequence match.

"mi/siRNA" refers to the practitioner's choice of either exogenous miRNA or siRNA to be administered to a cell. siRNAs derived from long dsRNA precursors differ from miRNAs in that miRNAs, especially those in animals, typically have incomplete base pairing to a target and inhibit the translation of many different mRNAs with similar sequences. In contrast, siRNAs typically base-pair perfectly and induce mRNA cleavage only in a single, specific target, although they may also induce miRNA-like off-target effects resulting in mRNA degradation of many off-targets.

"miRNA target sequence" refers to the sequence on a gene controlled by an endogenous miRNA that is targeted by this miRNA. Generally, there is a high degree of sequence similarity, although a perfect match is not necessary.

"endogenous miRNA sequence" refers to the sequence of the endogenous miRNA itself.

"Cell cycle genes" are genes that control the cell cycle that, when upregulated, may lead to tumorigenesis due to uncontrolled growth.

"RNA-induced silencing complex," or "RISC," is a multiprotein complex that incorporates one strand of a small interfering RNA (siRNA) as a template for recognizing complementary mRNA. When it finds a complementary strand, it activates RNase and cleaves the RNA. This process is important both in gene regulation by microRNAs. The RISC complex with a bound siRNA recognizes complementary messenger RNA (mRNA) molecules and degrades them, resulting in substantially decreased levels of protein translation and effectively turning off the gene. Endogenously expressed miRNA is usually imperfectly complementary to a large number of nuclear genes and has a modulating effect on these genes' levels of expression via translational repression.

RNA interference (RNAi) is a system within living cells that helps to control which genes are active and how active they are. Two types of small RNA molecules—microRNA (miRNA) and small interfering RNA (siRNA)—are central to RNA interference. RNAs are the direct products of genes, and these small RNAs can bind to specific other RNAs and either increase or decrease their activity, for example by preventing a messenger RNA from producing a protein. RNA interference has an important role in defending cells against parasitic genes—viruses and transposons—but also in directing development as well as gene expression in general.

The RNAi pathway is found in many eukaryotes including animals and is initiated by the enzyme Dicer, which cleaves long double-stranded RNA (dsRNA) molecules into short fragments of ~20 nucleotides. One of the two strands of each fragment, known as the guide strand, is then incorporated into the RNA-induced silencing complex (RISC). The most well-studied outcome is post-transcriptional gene silencing, which occurs when the guide strand base pairs with a complementary sequence of a messenger RNA molecule and induces cleavage by Argonaute, the catalytic component of the RISC complex. This process is known to spread systemically throughout the organism despite initially limited molar concentrations of siRNA.

The selective and robust effect of RNAi on gene expression makes it a valuable research tool, both in cell culture and in living organisms because synthetic dsRNA introduced into cells can induce suppression of specific genes of interest. RNAi may also be used for large-scale screens that systematically shut down each gene in the cell, which can help identify the components necessary for a particular cellular process or an event such as cell division. Exploitation of the pathway is also a promising tool in biotechnology and medicine.

RNAi is an RNA-dependent gene silencing process that is controlled by the RNA-induced silencing complex (RISC) and is initiated by short double-stranded RNA molecules in a cell's cytoplasm, where they interact with the catalytic RISC component argonaute. When the dsRNA is exogenous (coming from infection by a virus with an RNA genome or laboratory manipulations), the RNA is imported directly into the cytoplasm and cleaved to short fragments by the enzyme dicer. The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by dicer. Thus, the two dsRNA pathways, exogenous and endogenous, converge at the RISC complex.

Exogenous dsRNA initiates RNAi by activating the ribonuclease protein Dicer, which binds and cleaves double-stranded RNAs (dsRNA)s to produce double-stranded fragments of 21-25 base pairs with a few unpaired overhang bases on each end. Bioinformatics studies on the genomes of multiple organisms suggest this length maximizes target-gene specificity and minimizes non-specific effects. These short double-stranded fragments are called small interfering RNAs (siRNAs). These siRNAs are then separated into single strands and integrated into an active RISC complex. After integration into the RISC, siRNAs base-pair to their target mRNA and induce cleavage of the mRNA, thereby preventing it from being used as a translation template.

Exogenous dsRNA is detected and bound by an effector protein, known as RDE-4 in *C. elegans* and R2D2 in *Drosophila*, that stimulates dicer activity. This protein only binds long dsRNAs, but the mechanism producing this length specificity is unknown. These RNA-binding proteins then facilitate transfer of cleaved siRNAs to the RISC complex.

This initiation pathway may be amplified by the cell through the synthesis of a population of 'secondary' siRNAs using the dicer-produced initiating or 'primary' siRNAs as templates. These siRNAs are structurally distinct from dicer-produced siRNAs and appear to be produced by an RNA-dependent RNA polymerase (RdRP).

MicroRNAs (miRNAs) are genomically encoded non-coding RNAs that help regulate gene expression, particularly during development. The phenomenon of RNA interference, broadly defined, includes the endogenously induced gene silencing effects of miRNAs as well as silencing triggered by foreign dsRNA. Mature miRNAs are structurally similar to siRNAs produced from exogenous dsRNA, but before reaching maturity, miRNAs must first undergo extensive post-transcriptional modification. An miRNA is expressed from a much longer RNA-coding gene as a primary transcript known as a pri-miRNA which is processed, in the cell nucleus, to a 70-nucleotide stem-loop structure called a pre-miRNA by the microprocessor complex. This complex consists of an RNase III enzyme called Drosha and a dsRNA-binding protein Pasha. The dsRNA portion of this pre-miRNA is bound and cleaved by Dicer to produce the mature miRNA molecule that can be integrated into the RISC complex; thus, miRNA and siRNA share the same cellular machinery downstream of their initial processing.

The active components of an RNA-induced silencing complex (RISC) are endonucleases called argonaute proteins, which cleave the target mRNA strand complementary to their bound siRNA. As the fragments produced by dicer are double-stranded, they could each in theory produce a functional siRNA. However, only one of the two strands, which is known as the guide strand, binds the argonaute protein and directs gene silencing. The other anti-guide strand or passenger strand is degraded during RISC activation. Although it was first believed that an ATP-dependent helicase separated these two strands, the process is actually ATP-independent and performed directly by the protein components of RISC. The strand selected as the guide tends to be the one whose 5' end is least paired to its complement, but strand selection is unaffected by the direction in which dicer cleaves the dsRNA before RISC incorporation. Instead, the R2D2 protein may serve as the differentiating factor by binding the more-stable 5' end of the passenger strand.

It is not understood how the activated RISC complex locates complementary mRNAs within the cell. Although the cleavage process has been proposed to be linked to translation, translation of the mRNA target is not essential for RNAi-mediated degradation. Indeed, RNAi may be more effective against mRNA targets that are not translated. Argonaute proteins, the catalytic components of RISC, are localized to specific regions in the cytoplasm called P-bodies (also cytoplasmic bodies or GW bodies), which are regions with high rates of mRNA decay; miRNA activity is also clustered in P-bodies. Disruption of P-bodies decreases the efficiency of RNA interference, suggesting that they are the site of a critical step in the RNAi process.

Components of the RNA interference pathway are also used in many eukaryotes in the maintenance of the organisation and structure of their genomes. Modification of histones and associated induction of heterochromatin formation serves to downregulate genes pre-transcriptionally; this process is referred to as RNA-induced transcriptional silencing (RITS), and is carried out by a complex of proteins called the RITS complex. In fission yeast this complex contains argonaute, a chromodomain protein Chp1, and a protein called Tas3 of unknown function. As a consequence, the induction and spread of heterochromatic regions requires the argonaute and RdRP proteins. Indeed, deletion of these genes in the fission yeast *S. pombe* disrupts histone methylation and centromere formation, causing slow or stalled anaphase during cell division. In some cases, similar processes associated with histone modification have been observed to transcriptionally upregulate genes.

The mechanism by which the RITS complex induces heterochromatin formation and organization is not well understood, and most studies have focused on the mating-type region in fission yeast, which may not be representative of activities in other genomic regions or organisms. In maintenance of existing heterochromatin regions, RITS forms a complex with siRNAs complementary to the local genes and stably binds local methylated histones, acting co-transcriptionally to degrade any nascent pre-mRNA transcripts that are initiated by RNA polymerase. The formation of such a heterochromatin region, though not its maintenance, is dicer-dependent, presumably because dicer is required to generate the initial complement of siRNAs that target subsequent transcripts. Heterochromatin maintenance has been suggested to function as a self-reinforcing feedback loop, as new siRNAs are formed from the occasional nascent transcripts by RdRP for incorporation into local RITS complexes. The relevance of observations from fission yeast mating-type regions and centromeres to mammals is not clear, as heterochromatin maintenance in mammalian cells may be independent of the components of the RNAi pathway.

Results

Endogenous miRNA Targets are Upregulated Post miRNA Transfection

To investigate whether si/miRNA transfections affect gene regulation by endogenous miRNAs, we assembled data from small RNA transfection experiments followed by mRNA profiling and protein mass spectrometry. These data comprise more than 150 experiments from 7 different cell types, involving more than 20 different miRNAs and 40 unique siRNAs (Table 1). For each cell type, we used available miRNA expression profiles [20-22] to define the 10 most highly expressed endogenous miRNAs, which together make up 70-80% of the measured cellular miRNA content. Strikingly, a large number of genes are upregulated rather than downregulated in the si/miRNA experiments. We asked whether genes that are predicted targets of the cells' own (endogenous) miRNAs respond differently to the transfected si/miRNAs as compared to all other genes. In this analysis, we defined the set D of genes with predicted sites for 'enDogenous' miRNAs, the set X of predicted target genes of the 'eXogenous' si/miRNA, and a 'Baseline' set B of genes with neither endogenous nor exogenous sites. Differences in global expression changes between gene sets following si/miRNA transfection or miRNA inhibition were assessed for statistical significance by a one-sided Kolmogorov-Smirnov (KS) test (Methods).

Figure 3A:
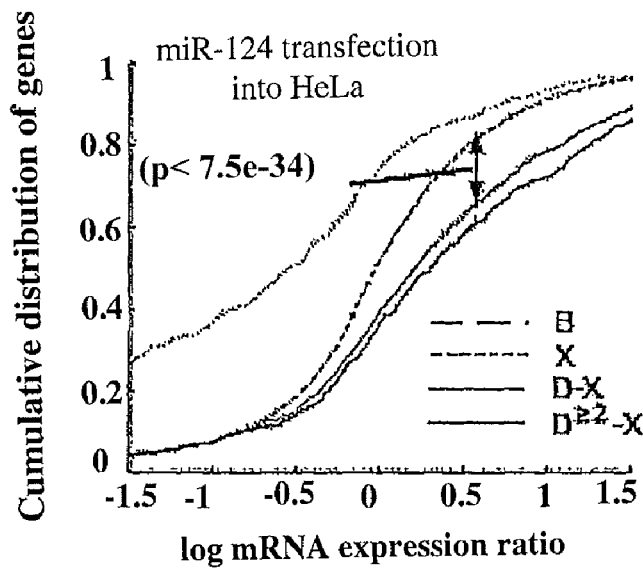
FIGS. 3A-F show visual representations of gene sets tested for significance in expression changes against baseline (B), where X is the set of genes with predicted sites for exogenous si/miRNAs, D-X is the set of genes with predicted sites for endogenous miRNA and no predicted sites for exogenous si/miRNAs, X-D is the set of genes containing exogenous sites and no endogenous site, X∩D is the set of genes with sites for both endogenous and exogenous miRNAs, $X-D^{\geq 2}$ is the set of genes containing exogenous sites but less than 2 endogenous sites, and $D^{\geq 2}-X$ is the set of genes containing at least 2 endogenous sites but no exogenous sites.

We found that in 90% of the experiments tested, the cumulative distribution of expression changes of the set of genes with endogenous target sites and no exogenous sites (D-X) was significantly up-shifted compared to the baseline set. For instance, when miR-124 is transfected into HeLa cells [23], genes with sites for HeLa-expressed (endogenous) miRNAs and no miR-124 sites are significantly upregulated compared to the baseline set ($p<7.5e-34$; FIG. 3A). The size of the effect is even more pronounced when we compare the upregulation of genes with at least 2 endogenous sites and no sites for the transfected miRNA to the baseline set ($p<2.2e-24$; FIG. 3A).

Figure 3B:
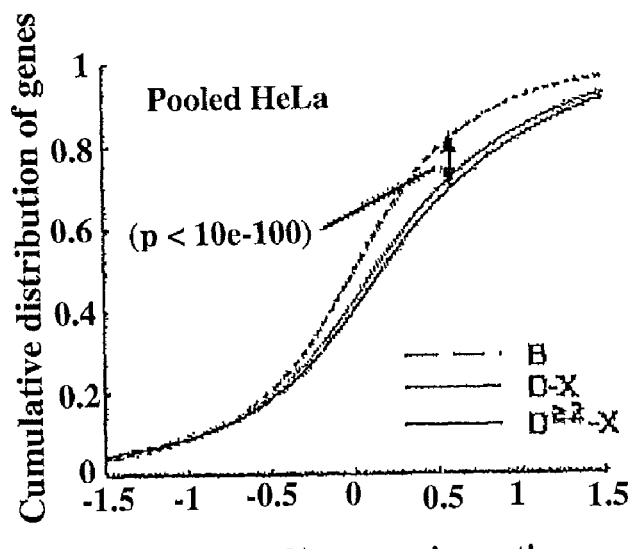

To see if the upregulation of genes with predicted sites for endogenous miRNAs was a general effect, we pooled all the HeLa transfection experiments and repeated the analysis. We found that the 'competition' effect is supported by the highly significant upregulation of the set D-X in the pooled HeLa data ($p<10^{-100}$; FIG. 3B). The same result is also true for pooled data in A549, HCT116, HCT116 Dicer$^{-/-}$ and Tov21G cells, with $p<10^{-10}$ for all cell types. Interestingly, over-expression of one endogenous miRNA also affects the targets of other endogenously expressed miRNAs. For example, in miR-16 and let-7b transfections into HeLa cells, the set D-X was upregulated compared to the baseline set ($p<5.6e-19$, $p<6.1e-12$ respectively).

As a positive control, we also compared the expression changes for the set of exogenous target genes (X) and the baseline gene set (B), both in individual transfection experiments and in sets of experiments grouped by cell type (Table 1). We found that the mRNA expression levels of target genes of the transfected small RNAs were significantly downshifted compared to the baseline set.

Figure 3C:
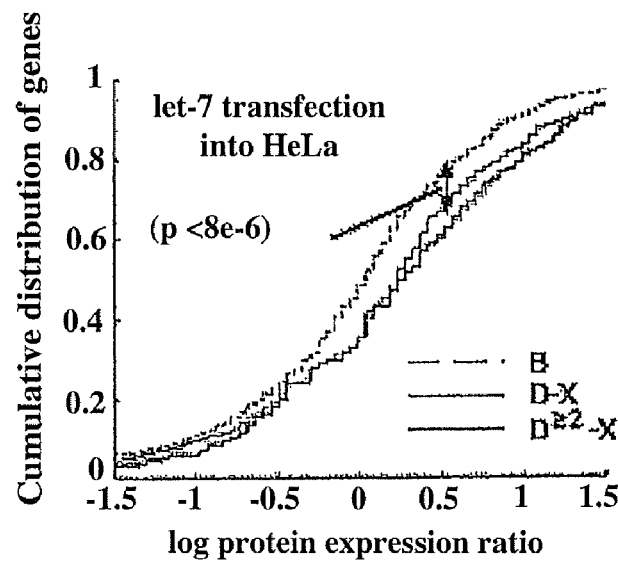

We also investigated protein expression levels in HeLa cells using data from mass spectrometry experiments following miRNA transfection [24] and found significant changes in protein expression following the five transfections. Target genes with sites for endogenous miRNAs and no sites for exogenous miRNAs (D-X) were upregulated in protein expression when compared to the baseline of genes with neither exogenous nor endogenous miRNA sites, ($p<1.3e-9$, pooled data). For example, transfection of let-7b into HeLa cells significantly increases protein expression of genes with other endogenous target sites only compared to the baseline gene set ($p<8e-6$; FIG. 3C).

siRNA Transfections Display the Same Effect as miRNA Transfections

Figure 3D:
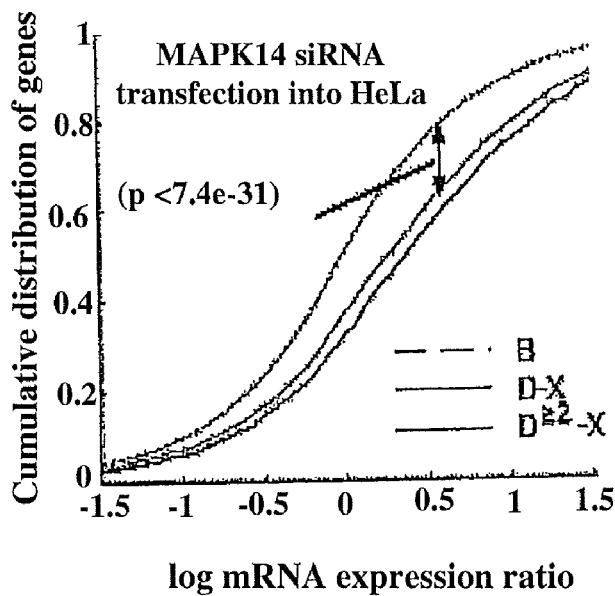

Next, we investigated 43 independent siRNA transfections in HeLa cells [19, 25, 26] to look for changes in regulation by endogenous miRNAs. We found (FIG. 3D) significant upregulation of gene expression after MAPK14-siRNA transfection for targets of endogenous miRNAs. Upregulation of let-7 and miR-15 targets, two miRNAs highly expressed in HeLa cells, was especially significant. Pooling the data from these siRNA experiments, we see a significant upward shift in expression of genes with endogenous sites only relative to the baseline gene set ($p<10^{-100}$). Five different siRNAs designed to target VHL, PRKCE, MPHOSPH1, SOS1, PIK3CA [26] all showed striking upregulation of highly similar sets of genes including CCND1, DUSP4, DUSP5, ATF3. Each one of these upregulated genes contains at least one site for an endogenous miRNA, consistent with upregulation as a consequence of the siRNA transfection, independent of the specific siRNA sequence.

Targets with Endogenous Sites are Less Downregulated than Expected

Figure 3E:
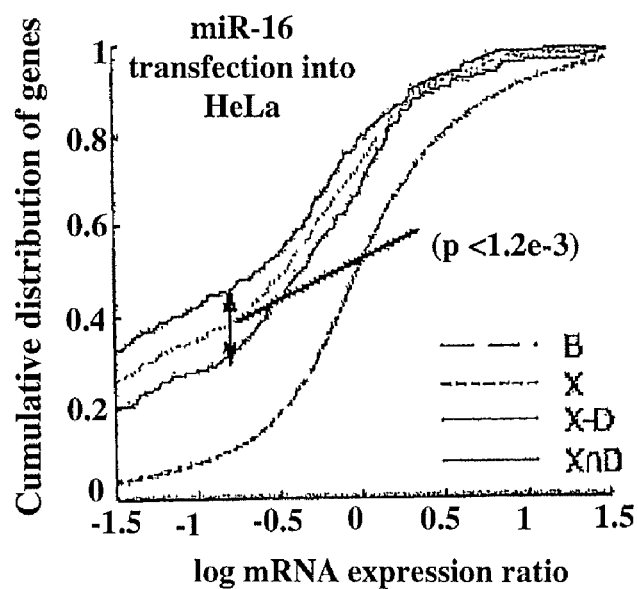
Figure 3F:
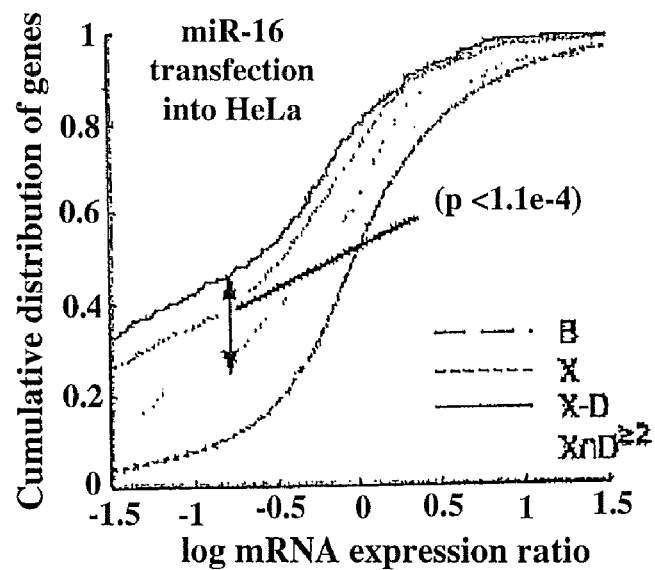

Next, we asked whether the response of genes directly targeted by the transfected si/miRNA also showed evidence of the competition effect. Specifically, we partitioned the set of genes with sites for transfected miRNAs (set X) into two subsets: genes with only exogenous sites and no endogenous sites (set X-D); and genes with both exogenous and endogenous sites (X∩D). After transfection of miR-16 into HeLa cells, genes with miR-16 target sites and no endogenous sites (FIG. 3E) are significantly more downregulated than target genes with endogenous sites (FIG. 3E), $p<1.2e-3$ (X-D vs. X∩D), with even greater difference when compared to genes with two or more sites for endogenous miRNAs ($p<1.1e-4$), FIG. 3F. Pooling data across a panel of transfection experiments into HeLa cells gave an even more significant result ($p<3.6e-13$).

A Quantitative Model Resolves the Endogenous miRNA Profile

Figure 4:
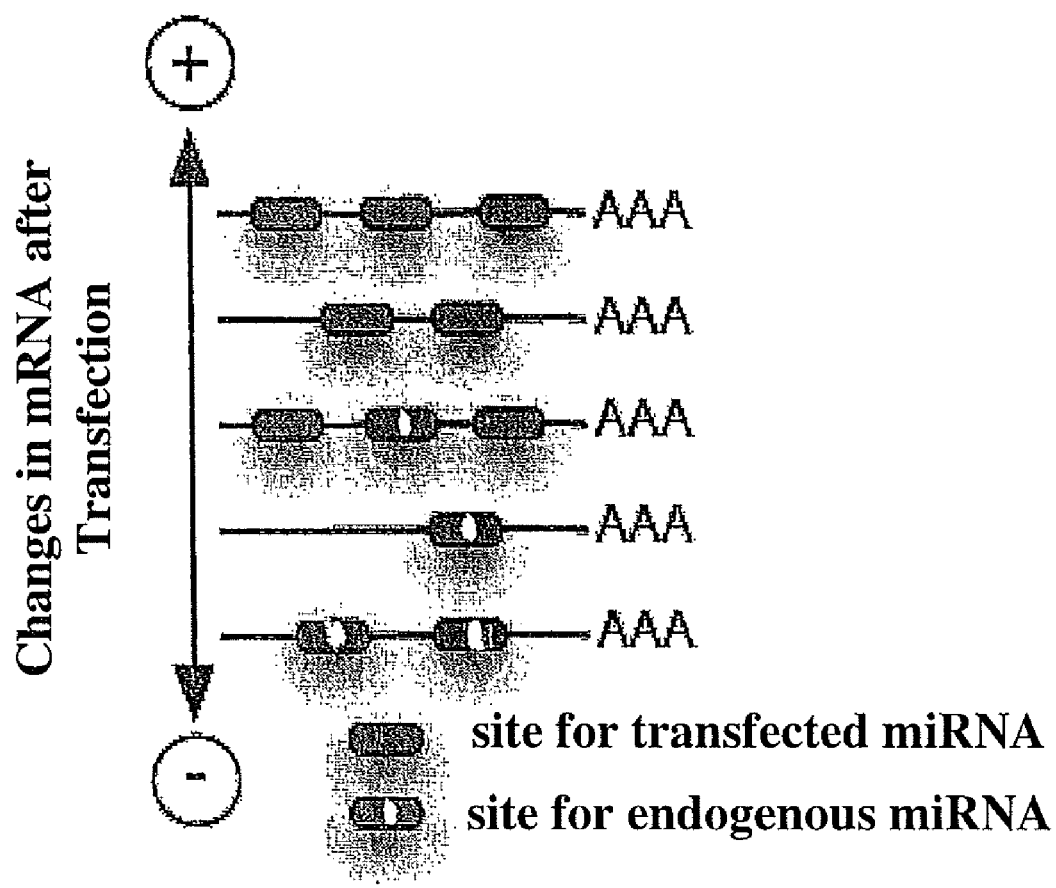
FIG. 4 is a cartoon graph of genes with different combinations of sites showing net effect on gene expression.

To strengthen our analysis and predict the saturation effect on individual genes, we built a quantitative mathematical model of the change in gene expression after si/miRNA transfection. This model can be used by the siRNA community to predict which genes are likely to be upregulated as well as downregulated (off-target effects) after si/miRNA transfections. Considering each transfection into HeLa cells independently, we first fit a simple linear regression model to predict the change in expression of genes from the number of exogenous sites ($n_X$) and the number of endogenous sites ($n_D$) in the 3' UTR of genes. In a large majority of experiments, the endogenous count $n_D$ was found to be a significant variable for explaining expression changes (84 out of 109 experiments satisfying $p<0.05$ by F statistic). The regression coefficient for the endogenous count was always positive when significant, meaning that these sites correlate with upregulation, while the regression coefficient for the exogenous count was always negative. FIG. 4 is a cartoon version of the effect on expression of a gene that contains different combinations of exogenous and endogenous sites.

We then refined the model to assess whether the presence of sites of individual miRNAs could explain upregulation of targets in an experiment, considering all human miRNA families as potential variables. We ranked the importance of each individual miRNA by the number of experiments in which it was included in a forward stepwise regression model. Among the 10 most frequently included miRNAs, we identified 7/10 of the most highly expressed miRNAs in a HeLa and 4/5 of the most highly expressed in HCT116 Dicer$^{-/-}$ cells, using no prior knowledge of the miRNA profile. The top ranked miRNAs retrieved by this analysis, let-7 and miR-21 are the most highly expressed miRNA in HeLa and HCT116 Dicer$^{-/-}$ cells respectively, and therefore strongly supports a saturation model. Indeed, taken altogether, these results suggest that the endogenous miRNA profile in a cell can largely be determined simply from expression changes after transfection of small RNAs, plausibly due to competition for cellular resources.

The Competition Effect has a Dose Response

Figure 5:
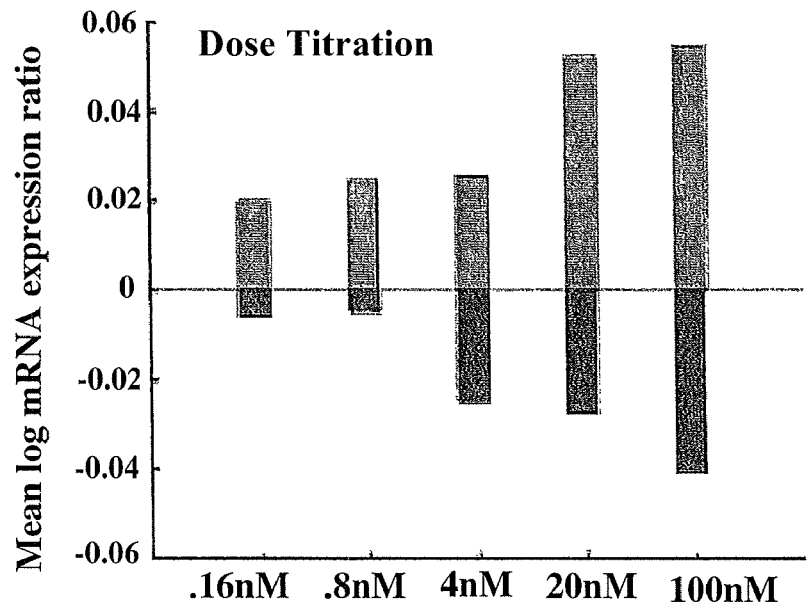
FIG. 5 shows a bar graph of the dose of siRNA transfection ranging 0.16 nM-100 nM versus mean log(expression change) in $X_{NC}$(grey) and $90^{th}$ percentile of $D_{NC}^{\geq 2}-X_{NC}$ (green).

In a previous study investigating siRNA dose response, a siRNA targeting MAPK14 was transfected into HeLa cells in a range of 5 doses, from 0.16 nM-100 nM, followed by microarray profiling after 24 hours [19]. We re-analyzed this data and confirmed the original analysis that the off-target effects of the siRNA mimic the dose response of the main target (MAPK14) and are not titrated away at lower transfection concentrations. However, there is also a set of upregulated genes that are consistently regulated in proportion to the dose of the siRNA (FIG. 5): genes with sites for endogenous miRNAs follow a pattern of upregulation that mirrors the downregulation of off-target genes with sites for the transfected siRNA in the 3' UTR. A 5-fold change in siRNA dose from 4 nM to 20 nM produces a 2-fold change in mean gene expression of the most responsive upregulated genes and the most responsive downregulated genes. The change in expression of both the endogenous target and off-target sets reaches near-maximal dose response at 20 nM; the saturation effect and siRNA off-target effects roughly scale with the dose response of the main target, at least for a significant fraction of genes in these sets, and cannot be titrated away at lower transfection concentrations.

Evidence for a Transitory Saturation Effect

We also examined the dynamics of the gene expression changes over 96 hours after siRNA transfections to measure the time dependence of the response of genes with sites for endogenous miRNAs. If genes under endogenous miRNA regulation are de-repressed the response should have a similar time progression as that of the intended siRNA target genes and its off-targets. We compared the mRNA changes of the putative off-target genes of the siRNA to the MAPK14 mRNA itself. Although the off-target genes of the siRNA (genes with non-conserved seed matches, $X_{NC}$) follow a temporal downregulation pattern similar to MAPK14 in the first 48 hours, the expression level of the $X_{NC}$ set of genes returns to near its original expression level by 92 hours. Indeed, the intended target MAPK14 has a gradually increasing downregulatory effect, with a half maximal effect seen at ~12 hours and a sustained effect from 24-96 hour.

Figure 6:
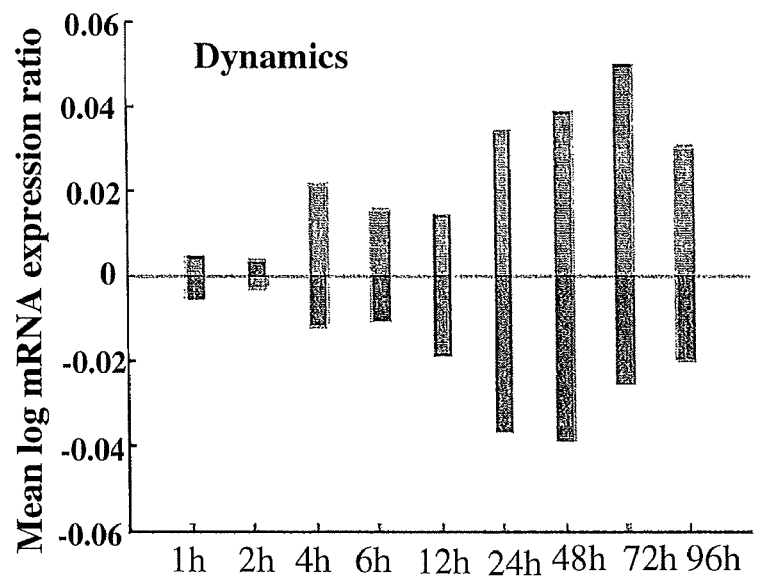
FIG. 6 is a bar graph of mean log(expression change) of $X_{NC}$(grey) and $90^{th}$ percentile of $D_{NC}^{\geq 2}-X_{NC}$ (green) versus time.

We investigated the dynamics of a set of genes with at least 2 non-conserved endogenous sites ($90^{th}$ percentile for expression change, pooling all time points, ~1000 genes), compared to a set of siRNA targeted genes. The genes in the endogenous set have maximal upregulation at 24-48 hours with similar dynamics across the 92 hours, consistent with being 'on-targets' of endogenous miRNAs competing for components of the RISC (FIG. 6). To examine particular examples, we compared the expression patterns of a set of the 6 most downregulated 'off-target genes' with 6 of the most upregulated genes in set $D_{NC}$-$X_{NC}$ and found strikingly similar temporal effects. The upregulated genes, SCML2, TNRC6, YOD1, CX3CL1, AKAP12, and PGM2L1, have maximal upregulation at 24-48 hours with similar dynamics across the 92 hours and contain at least 4 sites for highly expressed endogenous miRNAs. These genes are consistent with being 'on-targets' of endogenous miRNAs competing for components of the RISC. Notably, TNRC6 is associated with AGO2 in P-bodies.

We also investigated a recent set of experiments that were designed to examine the off-target effects of a therapeutic siRNA targeting APOB[18]. Our results showed a highly significant saturation effect with all 4 siRNAs designed to target the human APOB ($p<1e-8$ at 6 hours). We noticed that this siRNA effect reached its maximum effect at 6 hours, in line with the faster response time of the experiment as noted by the authors. The upregulated genes with sites for endogenous miRNAs also reached their maximum effect rapidly. Taken together these investigations of dynamics of small RNA gene regulation after transfection show that the upregulatory effect mirrors the downregulatory effect and supports the proposed competition model.

Cell Cycle Genes are Upregulated after si/miRNA Transfections

Dysregulation of endogenous miRNAs is known to contribute to tumorigenesis[27], and the experiments we analyzed were conducted in immortalized cell lines (e.g., HeLa cells). We were therefore not surprised to find a significant number of cell cycle, oncogene, and tumor suppressor genes consistently upregulated across transfection experiments. For instance, known miRNA targets, including the oncogene HMGA2 [28], CCND1 [29,30] and DUSP2 are upregulated after many different independent HeLa transfection experiments, including siRNA transfections. We also find that cell cycle genes are significantly enriched in endogenous miRNA target sites compared to other genes expressed in HeLa. Together, this suggests that cell cycle and oncogenes are particularly susceptible to the proposed saturation effect.

miRNA Inhibition May Cause Upregulation of Other Endogenous Targets

Finally, we examined mRNA expression changes after miRNA inhibition miR-16 and miR-106b 'antagomirs'[31], 2'-O-methyl inhibitors, produced a significant upregulation of genes which contained only endogenous sites, $p<5e-16$ (D-X) and $p<2e-30$ ($D^{22}$-X). There is a set of genes significantly de-repressed in both experiments, including, for example, SSR3, PLSCR4 and PTRF, although they contain no predicted sites for transfected inhibitors. They do, however, contain sites for endogenously expressed miRNAs, and so they serve as examples for the general effect that we observed statistically. Inhibition of miR-21 with LNA molecules [32] also produced significant upregulation of genes with sites for other endogenous miRNAs when compared with a saline transfection (p<2.5e-6). Elmen et al. observed dose-dependent accumulation of a shifted heteroduplex band, implying that the LNA-antimiR binds stably to the miRNA. This finding is consistent with hypothesis that the heteroduplex of miR-122::antimiR prevents the availability of free RISC machinery, but clearly more experiments are needed to distinguish between the possible models and assess the size of the inhibition effect on the function of endogenous miRNAs.

Discussion

This work tests the hypothesis that transfections of small RNAs can perturb endogenous miRNA function, subject to some limitations. In particular, this report does not attempt to resolve details of the mechanism behind the competition effect. The calculations of the effect, though carefully evaluated in statistical terms, are subject to the inaccuracies of miRNA target prediction, which entails both false positives and false negatives at the level of particular target genes. Arguments are presented in terms of overall distributions, rather than attempting to quantify the involvement of individual target sites in transfection-mediated expression changes. In future work, a number of quantitative criteria will determine the extent of the competition between exogenous and endogenous miRNAs and their effects on gene targeting. Quantitative detail will depend on knowing the concentration of the RISC complex and of other components of the small RNA machinery in the cell, the concentration of the transfected and endogenous miRNAs, the concentrations of the target mRNAs, and the number of actual targets in the cell for a specific small RNA, as well as kinetic parameters such as the on and off rates of small RNAs in the RNA-protein complexes. Models that posit different concentration-dependent and kinetic scenarios could help focus the range of experiments needed to quantify these effects.

In a quantitative approach, we built a regression model that can to a large extent recover the endogenous miRNA profile simply from the changes in gene expression following small RNA transfections. The purpose of this approach is not to infer the miRNA profiles per se but to provide independent strong evidence of the indirect perturbation of miRNA function. Finally, we used a series of published data to show that the dynamics and dose response of the genes affected by the proposed competition effect follow the same patterns as that of the genes directly targeted by the transfection.

We have shown that the expression of genes predicted to be under endogenous miRNA regulation is affected by small RNA transfection; that the effect is observable both at the mRNA and protein levels; and that it occurs following transfection of siRNAs designed to inhibit particular genes, as well as miRNA mimics and miRNA inhibitors introduced to test the biological effects of miRNAs. In a quantitative approach, we built a regression model that can to a large extent recover the endogenous miRNA profile simply from the changes in gene expression following small RNA transfections. The purpose of this approach is not to infer the miRNA profiles per se but to provide independent strong evidence of the indirect perturbation of miRNA function. Finally, we used a series of published data to show that the dynamics and dose response of the genes affected by the proposed competition effect follow the same patterns as that of the genes directly targeted by the transfection.

Without intending to be bound by any particular mechanism, the most plausible model for these observations is saturation of the RISC complex (or other necessary small RNA processing or transport machinery) and competition between the transfected small RNA and endogenous miRNA for binding (FIG. 1). Other models cannot be ruled out and may be consistent with the observed effect. While the precise mechanism of this competition effect remains to be established, the statistical significance of the observed shifts in transcript levels is clear, and the results of this analysis strongly support the thesis that small RNA transfections unexpectedly and unintentionally disturb gene regulation by endogenous miRNA.

These results have potentially important practical consequences for the use of siRNAs, as well as shRNAs, in functional genomics experiments. While it is already known that siRNAs can produce unwanted off-target effects, i.e. unintended downregulation of mRNAs via a partial sequence match between the siRNA and target, the effects observed here are distinct and involve the de-repression of miRNA-regulated genes.

These findings also have consequences for the development of miRNA target prediction methods, in two ways. First, as measuring mRNA expression changes after si/miRNA perturbations is a standard way to validate miRNA target prediction methods [23, 25, 33], one should take the saturation effect into consideration. Despite concerted efforts, bioinformatic si/miRNA target prediction methods still significantly over-predict the number of targets by at least 7 fold [24, 34-36]. Elegant work showing the dynamic (condition and cell-type dependent) regulation of UTR lengths [37] may explain some of these false positives, since shortening of UTRs may lead to loss of target sites, but is unlikely to explain all. The proposed competition effect may offer an explanation for false positive target prediction in cases where UTRs have target sites for both the transfected and endogenous miRNAs (FIG. 4). Second, as miRNAs may compete with each other, for target sites in mRNAs, the very idea of a 'target' mRNA should be re-assessed.

Further, the results have consequences for the development of small RNA therapeutics, considered to hold substantial promise [38]. miRNA inhibitors, e.g., anti-miR-122, have been used to target cholesterol synthesis [39] as well as HCV (hepatitis C virus) [39, 40] and HSV2 (herpes simplex virus) [41]. Therapeutic siRNAs have also been designed for potential treatment of cancer, including in melanoma, against VEGF-A/-C [42], and through anti-miR-21 in glioma [38, 43, 44]. This work illustrates the potentially broad consequences of the perturbation of the cell's miRNA activity profile after introduction of si/miRNA inhibitors and suggests that these effects be considered quantitatively during development of small RNA therapies. Experiments that quantify the relative concentrations of protein machinery and small RNAs in a particular cellular context, as well as a fuller exploration of the kinetics of the various binding events involved in small RNA biogenesis and function, are clearly required. This quantitative model implies a procedure for calibrating and potentially avoiding unwanted effects of the designed small RNA therapeutics.

Our work tests the hypothesis that transfections of small RNAs can perturb endogenous miRNA function, subject to some limitations. In particular, this report does not attempt to resolve details of the mechanism behind the competition effect. The calculations of the effect, though carefully evaluated in statistical terms, are subject to the inaccuracies of miRNA target prediction, which entails both false positives and false negatives at the level of particular target genes. We therefore argue in terms of overall distributions, rather than attempting to quantify the involvement of individual target sites in transfection-mediated expression changes. In future work, a number of quantitative criteria will determine the extent of the competition between exogenous and endogenous miRNAs and their effects on gene targeting. Quantitative detail will depend on knowing the concentration of the RISC complex and of other components of the small RNA machinery in the cell, the concentration of the transfected and endogenous miRNAs, the concentrations of the target mRNAs, and the number of actual targets in the cell for a specific small RNA, as well as kinetic parameters such as the on and off rates of small RNAs in the RNA-protein complexes. Models that posit different concentration-dependent and kinetic scenarios could help focus the range of experiments needed to quantify these effects.

Finally, our results may have an important biological correlate, as plausibly the competition effect may have a role in normal biological or disease-related cellular processes, e.g., in affecting miRNA-dependent regulatory programs. For example, during both differentiation and disease processes such as cancer, miRNA profiles can change dramatically both in the identity of the dominant miRNAs and in total cellular miRNA concentration. Such changes, via competition for limited resources, may orchestrate observable changes in cellular regulatory programs with potential physiological consequences.

In summary, the proposed and statistically supported competition effect for small RNAs may point to new biological mechanisms and likely has important practical consequences for the use of small RNAs in functional genomics experiments, for the development of miRNA target and siRNA off-target prediction methods, and for the development of small RNA therapeutics.

Methods mRNA and Protein Experimental Datasets

We collected data from four types of experiments: (i) transfection of a miRNA followed by mRNA profiling using microarrays [4, 23, 24, 29, 35, 45]; (ii) transfection of an siRNA followed by mRNA profiling [18, 19, 26]; (iii) inhibition of miRNA followed by mRNA profiling [32]; and (iv) transfection of miRNA followed by protein profiling using mass spectrometry [24]. These four types of data sets of 150 experiments encompass 7 different cell types, 20 different miRNAs, and 40 different siRNAs. The synthetic transfected miRNAs are all commercially available siRNA/miRNA mimics (Dharmacon, Inc.). Sequences of mimics can be found in the respective references. When possible, we used normalized microarray expression data as provided with the original publications. In all other cases, we used the "affy" package in the "R" software package to perform RMA normalization of microarray probe-level data. For statistical analysis over multiple mRNA microarray profiling experiments, each experiment was independently centered using the mean log(expression change) of genes lacking conserved endogenous or exogenous sites and normalized to have unit variance in log(expression change) across all genes. This normalization results in a modified Z-transformation of the data, where genes with no exogenous or endogenous sites have mean 0. For the transfection experiments followed by mass spectrometry, we used normalized protein expression levels as provided by the authors of the original publication.

Target Prediction

We conducted four different types of miRNA target site searches using miRNA sequences grouped into families, and 3' UTR alignment of 5 species. miRNAs were grouped into families as defined by identical nucleotides in positions 2-8. We searched for target sites for miRNA families in 3'UTRs using four different types of seed matches: (i) 6-mers (position 2-7 and 3-8), (ii) 7-mers (position 2-8), (iii) 7-mer positions 2-7 m1A (the first nucleotide an A in the mRNA) and (iv) 8-mers (position 1-8). 7-mer positions 2-8 were selected for analysis since this choice gave the most significant p-values for downregulation of targets with sites for the transfected si/miRNA based as compared to baseline genes based on a one-sided KS statistic (set X versus set B, as described below).

For target matches, we considered both non-conserved and conserved targets in human 3'UTRs. 3' UTR sequences for human (hg18), mouse (mm8), rat (rn4), dog (canFam2), and chicken (galGal2) were derived from RefSeq and the UCSC genome browser (hgdownload.cse.ucsc.edu/goldenPath/hg18/multiz17way/). We used multiple genome alignments across the 5 species as derived by multiZ. The RefSeq annotation with the longest UTR mapped to a single gene was always used. To establish a conservation filter, we required that the 7-mer target site in human be present in at least three of the other four species, i.e. exact matching in a 7 nucleotide window of the alignment in at least 3 other species, to be flagged as conserved. Restricting to conserved sites led to more significant p-values for downregulation of targets with exogenous sites as compared to baseline genes (one-sided KS statistic, set X versus set B, as defined below). We chose these stringent requirements so that our prediction method would be conservative and err on the side of under-prediction rather than over-prediction. However, we acknowledge that there are indeed functional siRNA and miRNA target sites that have mismatches, G:U wobbles in the 5' end and are not conserved (see for example work of the Hobert and Slack groups [46, 47]).

Endogenous miRNA Expression

We used endogenous miRNA profiles from the Landgraf et al [20] compendium for HeLa, A549, HepG2 and TOV21G, which provide relative miRNA expression levels from cloning and sequencing small RNA libraries. We used miRNA profiles from the Cummins et al [48] cloning and sequencing data for HCT116 and HCT116 Dicer$^{-/-}$. For consistency across cell types, we took the top 10 miRNAs with highest expression levels (clone counts), which corresponds to at least 75% of the miRNA content in each cell type, to be the set of endogenous miRNAs in our statistical analysis.

KS Statistics

To compare the expression changes for two gene sets, we compared their distributions of Z-transformed log(expression change) using a one-sided Kolmogorov-Smirnov (KS) statistic, which assesses whether the distribution of expression changes for one set is significantly shifted downwards (downregulated) compared to the distribution for the other set. We chose the KS statistic to apply a uniform treatment of data despite the heterogeneity of the transfection experiments, which involve different cell types, different numbers of target genes with sites for the transfected si/miRNA, and different apparent transfection efficiencies. The KS statistic has the advantages that (i) it is non-parametric and hence does not rely on distributional assumptions about expression changes; (ii) it does not rely on arbitrary thresholds; and (iii) it measures significant shifts between the entire distributions rather than just comparing the tails. The KS statistic computes the maximum difference in value of the empirical cumulative distribution functions (cdfs):

$$\sup_x (F_1(x) - F_2(x)),$$

where $$F_j(x) = \frac{1}{n_j} \sum_{i=1}^{n_j} I_{X_i \leq x}$$

is the empirical cdf for gene set j=1, 2, based on $n_j$ (Z-transformed) log(expression change) values. We used the Matlab function kstest2 to calculate the KS test statistic and asymptotic p-value.

Notation

We use the following notation to describe sets of genes based on the number of sites for exogenous and endogenous miRNAs in their 3'UTRs:

Non-conserved sites: sets with subscript $_{NC}$ denote non-conserved sites have been used; subscript $_{NC}^{\geq 2}$ denotes 2 or more non-conserved sites Endogenous sites: sites for endogenous miRNAs, i.e., miRNAs expressed in the cell Exogenous sites: sites for exogenous si/miRNAs, i.e., small RNAs introduced into the cell X ("eXogenous"): set of genes containing at least one site for the exogenous (transfected) si/miRNA D ("enDogenous"): set of genes containing at least one site for a miRNA endogenously expression in the cell type B ("Baseline"): set of genes containing neither exogenous nor endogenous sites D-X: set of genes containing at least one endogenous site and no exogenous sites X∩D: set of genes containing at least one exogenous site and at least one endogenous site X-D: set of genes containing at least one exogenous site and no endogenous sites $D^{32}$: set of genes containing 2 or more endogenous sites $X \cap D^{32}$: set of genes containing at least one exogenous site and at least 2 endogenous sites Regression Analysis to Model Expression We performed multiple linear regression to fit a linear model expressing the Z-transformed log(expression change), denoted as y, in terms of the number of a gene's exogenous and endogenous target sites, denoted as $n_X$ and $n_D$, respectively:

$$y = c_X n_X + c_D n_D + b.$$

We use the Matlab regress function to fit the model and assess the significance of the fit as measured by the $R^2$ statistic. We used the F statistic, also computed by the regress function, to assess whether the linear model with 2 independent variables, $n_X$ and $n_D$, significantly improves the fit over the simpler model: $y = c_X n_X + b$, given the number of sites for exogenous si/miRNAs a priori.

Forward Stepwise Regression Analysis

As an extension to the linear model with 2 independent variables, we performed forward stepwise regression to fit the number of target sites for each of the 162 miRNA families to the Z-transformed log(expression change) data. Starting again with the simpler model, $y = c_X n_X + b$, we incrementally added the number of target sites for the miRNA seed family with highest F statistic to the model. The procedure was continued until the p-value from the F-statistic for the best remaining seed family failed to satisfy a significance threshold of p<0.05. The final model can be viewed as a linear combination of the number exogenous target sites and the additive contribution of other miRNAs represented by their number of target sites $n_i$:

$$y = c_X n_X + \sum_i c_i n_i + b.$$

Since we did not enforce a stringent significance criterion for including miRNA sites in the model, we do not expect every miRNA added to the model to be correct; however, miRNAs added consistently across different transfections experiments are likely to be significant. We repeated the forward stepwise regression for multiple experiments in HeLa and HCT116 Dicer$^{-/-}$ cells and computed the frequency of the most statistically significant additive factors with positive regression coefficient in the model for each cell type; we reported the 10 most frequent of these miRNAs.

Cell Cycle and Cancer Genes

A list of expertly annotated genes for which mutations (both germline and somatic) have been causally implicated in cancer was obtained from the Cancer Genome Project (Cancer Gene Census catalogue version 2008.12.16, www.sanger.ac.uk/genetics/CGP/Census) [49]. A list of genes that have consistently showed a periodic expression pattern during the cell cycle in several mRNA microarray studies was obtained from the Cyclebase data base [50]. From these lists, we could match 312 and 651 genes to the mRNA data sets collected in this work, respectively. The gene sets were designated "oncogenes" and "cell cycle genes", respectively. To investigate if oncogenes or cell cycle genes were enriched for miRNA targets in Hela cells compared to all genes we used Fisher's exact tests.

A list of homo sapiens miRNA is available at microrna.sanger.ac.uk/cgi-bin/targets/v4/mirna.p1?genomeid_=2964 and micronaa.sanger.ac.uk/cgi-bin/sequences/mirna_summary.p1?org=hsa miRNA sequences for a variety of other species is available at microrna.sanger.ac.uk/sequences/. Targets for miRNA are found at microrna.sanger.ac.uk/targets/v5/Saturation Saturation Effect of Anti-APOB siRNA in Human Liver Cells Since small RNA therapeutics are currently most easily delivered to the liver, several pharmaceuticals are investigating siRNA and miRNA based therapies for liver diseases such as (i) hepatitis C and (ii) high LDL and cholesterol levels in the liver. Using published data from a study by Burchard et al. on siRNAs targeting the gene for apolipoprotein B (apoB), a protein involved in cholesterol metabolism, we examined whether there was evidence for saturation of RISC (or other small RNA machinery) due to small RNA transfections in a therapeutically relevant context.

We first identified the top 10 endogenously expressed small RNAs in HUH7 human hepatoma cell line using cloning and sequencing data from Landgraf et al.

| | | |
|---|---|---|
| TGGAGTGTGACAATGGTGTTTG | hsa-mir-122 | Seq ID No. 1 |
| TAGCTTATCAGACTGATGTTGA | hsa-mir-21 | Seq ID No. 2 |
| TAGCAGCACGTAAATATTGGCG | hsa-mir-16 | Seq ID No. 3 |
| CAGTGCAATGTTAAAAGGGCAT | hsa-mir-130a | Seq ID No. 4 |
| TGGCTCAGTTCAGCAGGAACAG | hsa-mir-24 | Seq ID No. 5 |
| AAGCTGCCAGTTGAAGAACTGT | hsa-mir-22 | Seq ID No. 6 |
| TTCACAGTGGCTAAGTTCTGC | hsa-mir-27b | Seq ID No. 7 |
| TTCAAGTAATCCAGGATAGGCT | hsa-mir-26a | Seq ID No. 8 |

-continued

| | | |
|---|---|---|
| CAACGGAATCCCAAAAGCAGCTG | hsa-mir-191 | Seq ID No. 9 |
| CTGACCTATGAATTGACAGCC | hsa-mir-192 | Seq ID No. 10 |

We predicted conserved targets of each miRNA if the (reverse complement) of the seed sequence (positions 2:8) occurred in the 3'UTRs of orthologous genes in human and mouse.

We analyzed published data from Burchard et al., infra in which siRNA duplexes designed to target the APOB gene were transfected in HUH7 cells at a concentration of 10 nM. The transfected cells were profiled by mRNA gene expression microarray at 6, 12, 24, and 48 hour time points. We predicted off-targets of the siRNAs if the (reverse complement) of the seed sequence (positions 2:8) occurred in 3'UTR of human genes.

| siRNA | seed sequence |
|---|---|
| APOB-Hs1 | ATTTTTC |
| APOB-Hs2 | AGTTATT |
| APOB-Hs3 | TTTCAGG |
| APOB-Hs4 | TGGTATT |

Examining the distribution of expression changes of predicted targets of endogenous miRNAs post siRNA transfection, we indeed found significant upregulation of the set of targets of the top 10 expressed miRNAs (p-value<2e-5 in 3 out of 4 experiments at 24 hours post transfection, KS test).

Since miR-122 is the most highly expressed endogenous miRNA in HUH7 and other liver derived cell lines (see Landgraf et al. [20]), we calculated the median upregulation of each predicted miR-122 target at the 24 hour time point in each siRNA transfection to identify genes that are potentially dysregulated due to saturation of the small RNA machinery.

Table 2 lists the top 20 predicted miR-122 target genes that are consistently upregulated at 24 hours in multiple experiments. Interestingly, many of these genes have been annotated to have some enzymatic function or are involved in cell-cell signaling/trafficking.

We calculated the potential saturation effects of therapeutic siRNAs designed against target genes in Amyotrophic lateral sclerosis (ALS, Lou Gehring's disease), age-related and diabetic macular degeneration (AMD), liver cancer and hypercholesterolemia.

| diseases | siRNA target | tissue used | top miRNA |
|---|---|---|---|
| age-related and diabetic macular degeneration (AMD) | Vegfr1 | (mouse eye) | miR-124, miR-16 |
| familial amyotrophic lateral sclerosis (ALS) | Sod1 | (human Frontal-cortex) | miR-9, miR-124 |
| liver cancer, hypercholesteremia | Vegf, ApoB | (human liver cells) | miR-122 |

In each case we identified genes which were strong predicted targets of highly expressed microRNAs expressed in the cell type of the disease target tissue. Tables 3-5 show lists of genes for each clinical target which are most likely to be upregulated after siRNA transfections in the targeted tissue. For instance, WSB2, XPR1 may be upregulated in liver cells after siRNA therapy in liver cancer and hypercholesteremia; similarly, SOCS5 and ONECUT2 may be upregulated in the frontal cortex after siRNA therapy against SOD1 in ALS patients. In addition we show that siRNAs directed against Sod1 result in the significant upregulation of endogenously microRNA-controlled genes. See FIG. 7.

TABLE 1

| | Cell type | Reference |
|---|---|---|
| Transfected microRNA | | |
| miR-124, miR-1, miR-373, miR-124mut5-6, miR-124mut9-10, chimiR-1-124, chimiR-124-1 | HeLa | Lim, L. P., et al., Microarray analysis shows that some microRNAs down-regulate large numbers of target mRNAs. Nature, 2005. |
| miR-106b, miR-200a/b, miR-141 miR-16, miR-15a/b, miR-103, miR-107, miR-192, miR-215, miR-17-5p, miR-20, let-7c, miR-195 | HeLa, HCT116 HCT116 Dicer$^{-/-}$ | Linsley, P. S., et al., Transcripts targeted by the microRNA-16 family cooperatively regulate cell cycle progression. Mol Cell Biol, 2007. |
| miR-7, miR-9, miR-122a, miR-128a, miR-132, miR-133a, miR-142, miR-148, miR-181a | HeLa | Grimson, A., et al., MicroRNA targeting specificity in mammals: determinants beyond seed pairing. Mol Cell, 2007. |
| miR-34a/b/c | HeLa, A549, TOV21G, HCT116 Dicer$^{-/-}$ | He, L., et al., A microRNA component of the p53 tumour suppressor network. Nature, 2007. |
| miR-1, miR-155, let-7, miR-30 | HeLa | Selbach, M., et al., Widespread changes in protein synthesis induced by microRNAs. Nature, 2008. |
| miR-181a, miR-124, miR-1 | HeLa | Baek, D., et al., The impact of microRNAs on protein output. Nature, 2008. |
| miR-34a | HeLa | Chang, T. C., et al., Transactivation of miR-34a by p53 broadly influences gene expression and promotes apoptosis. Mol Cell, 2007. |
| miR-124 | HepG2 | Wang, X. and X. Wang, Systematic identification of microRNA functions by combining target prediction and expression profiling. Nucleic Acids Res, 2006. |
| Transfected siRNA | | |
| igfr-1-16, mapk14-1-8, mapk14-1 (1, 2, 4, 6, 12, 24, 48, 72, 96) hours, mapk14-1 (.16, .8, 4, 20, 100) nM, makk14-1 (pos 4, 5, 15) mismatch | HeLa | Jackson A. L., et al., Expression profiling reveals off-target gene regulation by RNAi. Nature Biotechnology, 2003. |

TABLE 1-continued

| | Cell type | Reference |
|---|---|---|
| mphosph1-2692, pik3ca-2692, prkce-1295, vhl-2651, vhl-2652, sos1-1582 | HeLa | Jackson A. L., et al., Position-specific chemical modification of siRNAs reduces "off-target" transcript silencing. RNA, 2006. |
| pik3cb-6338, plk-1319, plk-772, pik3cb-6340 | HeLa | Jackson A. L., et al., Widespread siRNA "off-target" transcript silencing mediated by seed region sequence complementarity. RNA, 2006. |
| siApoB-Hs1/Hs2/Hs3/Hs4 | Huh7 | Burchard J, et al., MicroRNA-like off-target transcript regulation by siRNAs is species specific. RNA, 2009. |

TABLE 2

Genes likely to go up post-small RNA transfection in HUH7 cells (liver) due to endogenous targets of miR-122

| GENE NAME | MEDIAN NORMALIZED FOLD CHANGE |
|---|---|
| 'ANKRD13C' | 1.4 |
| 'BACH2' | 1.9898 |
| 'BCAT2' | 1.0804 |
| 'CDC25A' | 1.3273 |
| 'DLG2' | 1.2478 |
| 'FUNDC2' | 1.2562 |
| 'GLB1L' | 1.5867 |
| 'GNPDA2' | 2.7551 |
| 'IGSF5' | 1.2152 |
| 'IQGAP1' | 1.1237 |
| 'OCLN' | 1.4697 |
| 'PGM2L1' | 3.8057 |
| 'PRDM12' | 1.0604 |
| 'PRICKLE2' | 1.472 |
| 'RAB11FIP1' | 2.148 |
| 'SBK1' | 1.1789 |
| 'SIX3' | 1.0949 |
| 'SLC9A6' | 1.7202 |
| 'TMEM87A' | 1.4806 |
| 'XPR1' | 1.212 |

TABLE 3

Genes likely to go up post-small RNA transfection in mouse eye cells due to endogenous targets of miR-124 or miR-16

GENE NAME

'PAFAH1B1'
'PHF19'
'SKI'
'SLC7A1'
'SLC7A2'
'UBN2'
'CHIC1'
'CPD'
'CTDSP1'
'FAM123B'
'IP6K1'
'PLEKHM3'
'PSKH1'
'PTPN14'
'RAPH1'
'RASGEF1B'
'SMAD5'
'LUZP1'
'TNRC6B'
'APLN'

TABLE 4

Genes likely to go up post-small RNA transfection in human frontal cortex due to endogenous targets of miR-124 or miR-9

GENE NAME

'SLC39A9'
'SLC5A3'
'SNAI2'
'SOCS5'
'TNRC6B'
'TSPAN15'
'TWSG1'
'VAT1'
'ZDHHC3'
'ARFGEF2'
'CTDSP1'
'LDLRAP1'
'LPP'
'PLEKHM3'
'PRLR'
'PRTG'
'ROD1'
'SPTLC2'
'VAMP3'
'ONECUT2'

TABLE 5

Genes likely to go up post-small RNA transfection in human liver cells due to endogenous targets of miR-122

GENE NAME

'WSB2'
'XPR1'
'YARS'
'YKT6'
'ZBTB41'
'ZBTB7C'
'ZC3H10'
'ZDHHC24'
'ZDHHC3'
'ZDHHC7'
'ZYG11B'
'CD320'
'DULLARD'
'GRHL2'
'PMEPA1'
'SCN3B'
'SLC41A1'
'SLC7A1'
'SV2B'
'TMCC3'

In view of the foregoing, the present invention provides various advances over the art.

In some embodiments, the invention provides a method of choosing an exogenous mi/siRNA sequence to be applied to a cell for the purpose of downregulating a selected gene that takes into account endogenous miRNA target sequence(s). In accordance with the method, an exogenous mi/siRNA sequence is chosen that will target genes that contain the endogenous miRNA target sequence as well as the selected targets of the exogenous mi/siRNA sequence. In many cases, the sequences of genes and the endogenous miRNA that targets them are known, and the sequence of the selected gene is known in order to design the exogenous mi/siRNA, this may be a simple comparison of preexisting information. This method may be performed by determining the sequence of genes that are targeted by said endogenous miRNA sequence in a particular sample and choosing an mi/siRNA based on this determination.

The selection of an exogenous mi/siRNA that lacks a sequence match for the endogenous target sequence is anticipated in accordance with the present invention to result in enhanced expression of the endogenously regulated target gene as a consequence of the administration of the exogenous mi/siRNA. In contrast, the selection of an exogenous mi/is RNA that has a sequence match for the target sequence is anticipated in accordance with the present invention to exhibit enhanced expression of the target gene to a lesser extent, if at all.

In some embodiments of this method, the chosen exogenous mi/siRNA sequence is administered to cells. This administration may be in vivo, for a therapeutic purpose, or in vitro for further evaluation purposes.

In this embodiment, the method comprises the steps of:
identifying exogenous mi/siRNA that will inhibit expression of the selected gene;
comparing the sequence of at least one gene regulated by endogenous miRNA within the cell to the identified exogenous mi/siRNA; and,
based on the comparison of sequences, choosing from among the identified exogenous mi/siRNA a selected exogenous mi/siRNA.

As noted above, this approach can limit the amount of undesired disregulation of protein expression.

Of particular interest in this method in accordance with the invention is the avoidance of disregulation of an oncogene or a cell cycle gene. Thus, in accordance with the method of the invention, the proposed mi/siRNA sequences that will effect a target gene is compared with the sequences of at least one oncogene or cell cycle gene that is regulated by endogenous miRNA, and a selection of the exogenous mi/siRNA is made so that both the target gene (which can be any gene) and the at least one oncogene or cell cycle gene are both valid targets for the exogenous mi/siRNA.

A further embodiment of the invention is a method for method for monitoring and treating or simply treating the disregulation that can follow from mi/siRNA therapies. In accordance with this embodiment of the invention, genes that are upregulated by the administration of the exogenous mi/siRNA to cells of a given type are identified, and the individual is treated for example using a secondary therapeutic such as an antisense or siRNA therapeutic targeted to the up-regulated gene. In some embodiments, the treatment is applied prophylactically based on the experience of genes that are identified as likely to be upregulated in a given cell type. This can be accomplished using the procedures outlined above. In other embodiments, an individual receiving mi/siRNA therapy could be tested for disregulation and then treated.

In the case were testing is to be performed, the testing may be performed using a kit. In one embodiment, such a kit comprises a marker for endogenous miRNA regulated genes that facilitates the expression level of these genes in a tested sample. For specific cell types, the kit may include a plurality of markers for a plurality of genes overexpressed in that cell type. In specific embodiments, the lit also includes a sequence comparator to identify those endogenous miRNA regulated genes with and without a sequence match the exogenous mi/siRNA. In an embodiment, this kit includes reagents for delivering exogenous mi/siRNA sequences to a cell, for example exogenous sequences that the downregulate the overexpressed genes.

The present invention also provides a method for determining the potential for unwanted upregulation of genes as a result of mi/siRNA treatment on a cell. This method comprises the steps of
determining the number of endogenous miRNA target sites on genes expressed by the cell; and,
correlating a relatively higher number of endogenous miRNA target sites with a higher likelihood of unwanted upregulation of genes containing endogenous miRNA target sites.

In some embodiments, the method for determining the potential for unwanted upregulation, further comprises the step of determining endogenous miRNA expressed by the cell. In this case, the correlating step indicates a higher likelihood of unwanted upregulation of genes containing a higher number of target sites for endogenous miRNA that are actually expressed by the cell.

The results of this method can be used in determining a course of treatment where there is a high likelihood of unwanted upregulation of genes as a result of mi/siRNA treatment. In accordance with this aspect of the invention, an exogenous mi/siRNA sequence is preferred that will target genes with the endogenous miRNA target as well as desired targets of the exogenous mi/siRNA sequence if a higher likelihood of unwanted upregulation of genes is determined.

The potential for unwanted upregulation of genes can also be countered through the selection of an appropriate dosage of exogenous mi/siRNA. Thus, the invention also provides a method for determining a dosage of exogenous mi/siRNA to be administered to a cell, where the dosage is one that will reduce unwanted endogenous upregulation. The method comprises the steps of
determining the number of endogenous miRNA target sites on genes expressed by the cell; and,
administering an amount of exogenous mi/siRNA consistent with the number of endogenous miRNA target sites wherein less mi/siRNA is administered if more endogenous miRNA target sites are found. It will be appreciated that the determined dosage is a "tolerable" dosage that balances the off-target effects with the desired therapeutic effects.

Finally, the invention provides a upregulating a gene controlled by endogenous miRNA using a process that is the opposite of that discussed above. In this case, the method comprises the steps of
identifying miRNA target sequences within the gene that is controlled by endogenous miRNA that are expressed by the cell; and,
administering an exogenous mi/siRNA that does not target the gene, in an amount sufficient to upregulate the gene.

In practicing the method of the invention, various techniques that are known in the art are suitably employed.

For detection and identification of endogenous miRNA sequences, there are existing resources profiling the miRNAs expressed in many human cell types, including a recent mammalian miRNA expression atlas based on sequencing over 250 small RNA libraries from 26 different organ systems and cell types in human, mouse and rat (Landgrafr et al, Cell 2007). Identification of the top 10 endogenously expressed miRNAs (which typically account for 70-80% of all expressed miRNAs in the cell) is sufficient for determination of depression effects due to saturation after si/miRNA transfection. In cell types not covered by existing miRNA expression data sets, the endogenous miRNA profile can be determined by standard assays such as miRNA microarrays, multiplex RT-PCR assays, and deep sequencing of small RNAs.

For detecting/identifying endogenous miRNA target sequences, miRNA targets are commonly predicted by bioinformatics algorithms, the simplest of which is the identification of conserved seed matches (regions complementary to the 7-mer seed region at positions 2-8 of the miRNA) in the 3' UTR sequences of mRNAs (Khan et al, Nature Biotechnology 2009). Existing miRNA target prediction algorithms include TargetScan (www.targetscan.org/), PicTar (pictar.mdc-berlin.de/), and miRanda and mirSVR (www.microrna.org/). Specific targets genes proteins in cells can be detected and/or quantified using known procedures, including various blot procedures and antibody procedures.

For purposes of identifying exogenous mi/siRNA that will inhibit expression of a selected gene, there is a wide literature on design of siRNAs to target a selected gene. The general design guidelines describe sequence rules for determining favorable siRNA target site sequences in the 3' UTR of the selected gene. siRNAs are designed to have high complementary to their target sequences, and typically 2-4 target sequences are chosen. siRNAs against a wide number of human, mouse and rat genes are commercially available.

This step is performed with computational miRNA target prediction. Determination of the genes expressed in a given cell type can be done using mRNA expression profiling with microRNAs or newer sequencing methods such as RNA-seq or digital gene expression (DGE).

REFERENCES

1. Ruvkun, G., The perfect storm of tiny RNAs. Nat Med, 2008. 14(10): p. 1041-5.
2. Ambros, V., The functions of animal microRNAs. Nature, 2004. 431(7006): p. 350-5.
3. Filipowicz, W., S. N. Bhattacharyya, and N. Sonenberg, Mechanisms of post-transcriptional regulation by microRNAs: are the answers in sight? Nat Rev Genet, 2008. 9(2): p. 102-14.
4. He, L. and G. J. Harmon, MicroRNAs: small RNAs with a big role in gene regulation. Nat Rev Genet, 2004. 5(7): p. 522-31.
5. Tam, W., The emergent role of microRNAs in molecular diagnostics of cancer. J Mol Diagn, 2008. 10(5): p. 411-4.
6. Rossi, J., P. Zamore, and M. A. Kay, Wandering eye for RNAi. Nat Med, 2008. 14(6): p. 611.
7. Leachman, S. A., et al., Therapeutic siRNAs for dominant genetic skin disorders including pachyonychia congenita. J Dermatol Sci, 2008. 51(3): p. 151-7.
8. Robbins, M., et al., Misinterpreting the therapeutic effects of siRNA caused by immune stimulation. Hum Gene Ther, 2008.
9. Grimm, D., et al., Fatality in mice due to oversaturation of cellular microRNA/short hairpin RNA pathways. Nature, 2006. 441(7092): p. 537-41.
10. Stewart, C. K., J. Li, and S. P. Golovan, Adverse effects induced by short hairpin RNA expression in porcine fetal fibroblasts. Biochem Biophys Res Commun, 2008. 370(1): p. 113-7.
11. McBride, J. L., et al., Artificial miRNAs mitigate shRNA-mediated toxicity in the brain: implications for the therapeutic development of RNAi. Proc Natl Acad Sci USA, 2008. 105(15): p. 5868-73.
12. John, M., et al., Effective RNAi-mediated gene silencing without interruption of the endogenous microRNA pathway. Nature, 2007. 449(7163): p. 745-7.
13. Vankoningsloo, S., et al., Gene expression silencing with 'specific' small interfering RNA goes beyond specificity—a study of key parameters to take into account in the onset of small interfering RNA off-target effects. Febs J, 2008. 275(11): p. 2738-53.
14. Castanotto, D., et al., Combinatorial delivery of small interfering RNAs reduces RNAi efficacy by selective incorporation into RISC. Nucleic Acids Res, 2007. 35(15): p. 5154-64.
15. Gruber, J., et al., RNAi of FACE1 protease results in growth inhibition of human cells expressing lamin A: implications for Hutchinson-Gilford progeria syndrome. J Cell Sci, 2005. 118(Pt 4): p. 689-96.
16. Wargelius, A., S. Ellingsen, and A. Fjose, Double-stranded RNA induces specific developmental defects in zebrafish embryos. Biochem Biophys Res Commun, 1999. 263(1): p. 156-61.
17. Oates, A. C., A. E. Bruce, and R. K. Ho, Too much interference: injection of double-stranded RNA has non-specific effects in the zebrafish embryo. Dev Biol, 2000. 224(1): p. 20-8.
18. Burchard, J., et al., MicroRNA-like off-target transcript regulation by siRNAs is species specific. Rna, 2009. 15(2): p. 308-15.
19. Jackson, A. L., et al., Expression profiling reveals off-target gene regulation by RNAi. Nat Biotechnol, 2003. 21(6): p. 635-7.
20. Landgraf, P., et al., A mammalian microRNA expression atlas based on small RNA library sequencing. Cell, 2007. 129(7): p. 1401-14.
21. He, L., et al., A microRNA component of the p53 tumour suppressor network. Nature, 2007. 447(7148): p. 1130-4.
22. Cummins, J. M., et al., The colorectal microRNAome. Proc Natl Acad Sci USA, 2006. 103(10): p. 3687-92.
23. Lim, L. P., et al., Microarray analysis shows that some microRNAs downregulate large numbers of target mRNAs. Nature, 2005. 433(7027): p. 769-73.
24. Selbach, M., et al., Widespread changes in protein synthesis induced by microRNAs. Nature, 2008.
25. Jackson, A. L., et al., Widespread siRNA "off-target" transcript silencing mediated by seed region sequence complementarity. Rna, 2006. 12(7): p. 1179-87.
26. Jackson, A. L., et al., Position-specific chemical modification of siRNAs reduces "off-target" transcript silencing. Rna, 2006. 12(7): p. 1197-205.
27. Ventura, A. and T. Jacks, MicroRNAs and cancer: short RNAs go a long way. Cell, 2009. 136(4): p. 586-91.
28. Mayr, C., M. T. Hemann, and D. P. Bartel, Disrupting the pairing between let-7 and Hmga2 enhances oncogenic transformation. Science, 2007. 315(5818): p. 1576-9.
29. Linsley, P. S., et al., Transcripts targeted by the microRNA-16 family cooperatively regulate cell cycle progression. Mol Cell Biol, 2007. 27(6): p. 2240-52.
30. Bonci, D., et al., The miR-15a-miR-16-1 cluster controls prostate cancer by targeting multiple oncogenic activities. Nat Med, 2008. 14(11): p. 1271-7.
31. Krutzfeldt, J., et al., Silencing of microRNAs in vivo with 'antagomirs'. Nature, 2005. 438(7068): p. 685-9.
32. Elmen, J., et al., Antagonism of microRNA-122 in mice by systemically administered LNA-antimiR leads to up-regulation of a large set of predicted target mRNAs in the liver. Nucleic Acids Res, 2008. 36(4): p. 1153-62.

33. Jackson, A. L. and P. S. Linsley, Noise amidst the silence: off-target effects of siRNAs? Trends Genet, 2004. 20(11): p. 521-4.
34. Baek, D., et al., The impact of microRNAs on protein output. Nature, 2008.
35. Grimson, A., et al., MicroRNA targeting specificity in mammals: determinants beyond seed pairing. Mol Cell, 2007. 27(1): p. 91-105.
36. John, B., et al., Human MicroRNA targets. PLoS Biol, 2004. 2(11): p. e363.
37. Sandberg, R., et al., Proliferating cells express mRNAs with shortened 3' untranslated regions and fewer microRNA target sites. Science, 2008. 320(5883): p. 1643-7.
38. Stenvang, J., M. Lindow, and S. Kauppinen, Targeting of microRNAs for therapeutics. Biochem Soc Trans, 2008. 36(Pt 6): p. 1197-200.
39. Fabani, M. M. and M. J. Gait, miR-122 targeting with LNA/2'-O-methyl oligonucleotide mixmers, peptide nucleic acids (PNA), and PNA-peptide conjugates. Rna, 2008. 14(2): p. 336-46.
40. Lupberger, J., L. Brino, and T. F. Baumert, RNAi: a powerful tool to unravel hepatitis C virus-host interactions within the infectious life cycle. J Hepatol, 2008. 48(3): p. 523-5.
41. Palliser, D., et al., An siRNA-based microbicide protects mice from lethal herpes simplex virus 2 infection. Nature, 2006. 439(7072): p. 89-94.
42. Shibata, M. A., et al., Combination therapy with short interfering RNA vectors against VEGF-C and VEGF-A suppresses lymph node and lung metastasis in a mouse immunocompetent mammary cancer model. Cancer Gene Ther, 2008. 15(12): p. 776-86.
43. Elmen, J., et al., LNA-mediated microRNA silencing in non-human primates. Nature, 2008. 452(7189): p. 896-9.
44. Corsten, M. F., et al., MicroRNA-21 knockdown disrupts glioma growth in vivo and displays synergistic cytotoxicity with neural precursor cell delivered S-TRAIL in human gliomas. Cancer Res, 2007. 67(19): p. 8994-9000.
45. Chang, T. C., et al., Transactivation of miR-34a by p53 broadly influences gene expression and promotes apoptosis. Mol Cell, 2007. 26(5): p. 745-52.
46. Vella, M. C., K. Reinert, and F. J. Slack, Architecture of a validated microRNA::target interaction. Chem Biol, 2004. 11(12): p. 1619-23.
47. Didiano, D. and O. Hobert, Molecular architecture of a miRNA-regulated 3' UTR. Rna, 2008. 14(7): p. 1297-317.
48. Cummins, J. M. and V. E. Velculescu, Implications of micro-RNA profiling for cancer diagnosis. Oncogene, 2006. 25(46): p. 6220-7.
49. Futreal, P. A., et al., A census of human cancer genes. Nat Rev Cancer, 2004. 4(3): p. 177-83.
50. Gauthier, N. P., et al., Cyclebase.org—a comprehensive multi-organism online database of cell-cycle experiments. Nucleic Acids Res, 2008. 36(Database issue): p. D854-9.

All references cited herein are hereby incorporated by reference.

What is claimed is:

1. A method for determining the potential for unwanted upregulation of non-target genes as a result of exogenous miRNA or siRNA treatment on a cell, wherein the exogenous miRNA or siRNA treatment is directed to a target gene, and wherein the non-target genes are genes, different from the target gene, that are subject to downregulation by endogenous miRNA in the cell, comprising:

determining the number of endogenous miRNA target sites on genes expressed by the cell; and, correlating a relatively higher number of endogenous miRNA target sites with a higher likelihood of unwanted upregulation of non-target genes as a result of competition with endogenous miRNA for or saturation of RISC machinery by the exogenous miRNA or siRNA.

2. The method of claim 1, further comprising identifying endogenous miRNA expressed by the cell, and wherein the correlating step further indicates a higher likelihood of unwanted upregulation as a result of the exogenous miRNA or siRNA treatment on the cell of genes containing a higher number of target sites for the endogenous miRNA expressed by the cell.

3. The method of claim 1, wherein the unwanted upregulation of non-target genes is upregulation of an oncogene or a cell cycle gene.

* * * * *